United States Patent
Singh et al.

(10) Patent No.: US 11,453,895 B1
(45) Date of Patent: Sep. 27, 2022

(54) ENGINEERED HOSTS WITH EXOGENOUS LIGNINASE AND USES THEREOF

(71) Applicant: National Technology & Engineering Solutions of Sandia, LLC, Albuquerque, NM (US)

(72) Inventors: Seema Singh, Tracy, CA (US); Arul Mozhy Varman, Tempe, AZ (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 13 days.

(21) Appl. No.: 16/838,340

(22) Filed: Apr. 2, 2020

Related U.S. Application Data

(60) Provisional application No. 62/829,182, filed on Apr. 4, 2019.

(51) Int. Cl.
| | | |
|---|---|---|
| *C08H 7/00* | (2011.01) | |
| *C07G 1/00* | (2011.01) | |
| *C12N 9/02* | (2006.01) | |
| *C12N 9/08* | (2006.01) | |
| *C12N 1/21* | (2006.01) | |
| *C12P 7/10* | (2006.01) | |

(52) U.S. Cl.
CPC ............... *C12P 7/10* (2013.01); *C07G 1/00* (2013.01); *C08H 6/00* (2013.01); *C12N 9/0061* (2013.01); *C12N 9/0065* (2013.01); *C12Y 110/03002* (2013.01); *C12Y 111/01016* (2013.01)

(58) Field of Classification Search
None
See application file for complete search history.

(56) References Cited

U.S. PATENT DOCUMENTS

| | | |
|---|---|---|
| 7,485,343 B1 | 2/2009 | Branson et al. |
| 8,481,974 B1 | 7/2013 | Davis et al. |
| 9,765,044 B2 | 9/2017 | Socha et al. |
| 10,112,916 B2 | 10/2018 | Sathitsuksanoh et al. |
| 10,155,735 B2 | 12/2018 | Socha et al. |
| 10,208,076 B2 | 2/2019 | Singh et al. |
| 10,233,292 B2 | 3/2019 | Singh et al. |
| 10,240,180 B2 | 3/2019 | Northen et al. |
| 2014/0123404 A1* | 5/2014 | Wang .................. D06L 4/40 8/401 |

FOREIGN PATENT DOCUMENTS

CN 103321074 A * 9/2013

OTHER PUBLICATIONS

Larsson et al., Development of a *Saccharomyces cerevisiae* Strain with Enhanced Resistance to Phenolic Fermentation Inhibitors in Lignocellulose Hydrolysates by Heterologous Expression of Laccase, Appl. Environ. Microbiol. 67, 2001, 1163-70. (Year: 2001).*
Cassland et al., Characterization of a gene encoding Trametes versicolor laccase A and improved heterologous expression in *Saccharomyces cerevisiae* by decreased cultivation temperature, Appl. Microbiol. Biotechnol. 52, 1999, 393-400. (Year: 1999).*
Gonzalez-Perez et al., Assembly of evolved ligninolytic genes in *Saccharomyces cerevisiae*, Bioengineered 5, 2014, 254-63. (Year: 2014).*
Uniprot, Accession No. 094753, 2018, www.uniprot.org. (Year: 2018).*
Uniprot, Accession No. Q9HDQ0, 2018, www.uniprot.org. (Year: 2018).*
Lu-Chau et al., Effect of pH on the stability of Pleurotus eryngii versatile peroxidase during heterologous production in Emericella nidulans, Bioprocess Biosyst Eng. 26, 2004, 287-9. (Year: 2004).*
Fillat et al., Laccases as a Potential Tool for the Efficient Conversion of Lignocellulosic Biomass: A Review, Fermentation 3, 2017, 17. (Year: 2017).*
Puigbo et al., OPTIMIZER: a web server for optimizing the codon usage of DNA sequences, Nucleic Acid Res. 35 , 2007, W126-W131). (Year: 2007).*
Guo et al., Protein tolerance to random amino acid change, Proc. Natl. Acad. Sci. USA 101, 2004, 9205-10. (Year: 2004).*
Garcia-Ruiz et al., Directed evolution of a temperature-, peroxide- and alkaline pH-tolerant versatile peroxidase, Biochem. J. 441, 2012, 487-98. (Year: 2012).*
Mate et al., Blood tolerant laccase by directed evolution, Chem. Biol. 20, 2013, 223-31. (Year: 2013).*
Mate et al., Laboratory evolution of high-redox potential laccases, Chem. Biol. 17, 2010, 1030-41. (Year: 2010).*
GenBank, Accession No. CAA78144.1, 2006, www.ncbi.nlm.nih.org. (Year: 2006).*
Weiss et al., Enzymatic lignocellulose hydrolysis, Biotechnol. Biofuel 6, 2013, 5. (Year: 2013).*
GenBank, Accession No. ACY82388.1, 2016, www.ncbi.nlm.nih.gov. (Year: 2016).*
Bao et al., Improvement of hydrogen peroxide stability of Pleurotus eryngii versatile lignolytic peroxidase by rational protein engineering, Enz. Microbial Technol. 54, 2014, 51-58. (Year: 2014).*
GenBank, Accession No. AF007222.1, 2003, www.ncbi.nlm.gov. (Year: 2003).*
Nicolini et al., Recombinant laccase, J. Cellular Biochem. 114, 2013, 599-605. (Year: 2013).*
Barber-Zucker et al., Stable and Functionally Diverse Versatile Peroxidases Designed Directly from Sequences, J. Am. Chem. Soc. 144, 2022, 3564-71. (Year: 2022).*

(Continued)

*Primary Examiner* — Robert B Mondesi
*Assistant Examiner* — Todd M Epstein
(74) *Attorney, Agent, or Firm* — Samantha Updegraff; Weaver Austin Villeneuve & Sampson LLP

(57) ABSTRACT

The present invention relates to methods and engineered microbial hosts useful for treating lignin or a derivative thereof. In some embodiments, the host has one or more exogenous nucleic acid sequences that encode a ligninase (e.g., a laccase and/or a peroxidase).

20 Claims, 10 Drawing Sheets

Specification includes a Sequence Listing.

(56) References Cited

OTHER PUBLICATIONS

Alcade M, "Engineering the ligninolytic enzyme consortium," Trends Biotechnol. 2015;33:155-162.
Alcade M, "Laccases: Biological Functions, Molecular Structure and Industrial Applications," Chapter 26 in Industrial Enzymes (J. Polaina and AP MacCabe, eds.), Springer (Dordrecht, the Netherlands), 2007, pp. 461-476.
Brockmeier U et al., "Systematic screening of all signal peptides from Bacillus subtilis: a powerful strategy in optimizing heterologous protein secretion in Gram-positive bacteria," J. Molec. Biol. 2006;362(3):393-402.
Camarero S et al., "Engineering platforms for directed evolution of laccase from Pycnoporus cinnabarinus," Appl. Environ. Microbiol. 2012;78:1370-84.
Dashtban M et al., "Fungal biodegradation and enzymatic modification of lignin," Int. J. Biochem. Mol. Biol. 2010;1:36-50.
Desai SS et al., "Microbial laccases and their applications: a review," Asian J. Biotechnol. 2011;3:98-124.
Falade AO et al., "Lignin peroxidase functionalities and prospective applications," Microbiol. Open 2017;6:e00397 (14 pp.).
Fisher AB et al., "Lignin biodegradation and industrial applications," AIM Bioeng. 2014;1:92-112.
Garcia-Ruiz E et al., "Directed evolution of a temperature, peroxide and alkaline pH tolerant versatile peroxidase," Biochem. J. 2012;441:487-98.
Gonzalez-Perez D et al., "Alkaline versatile peroxidase by directed evolution," Catal. Sci. Technol. 2016;6:6625-36.
Gonzalez-Perez D et al., "Assembly of evolved ligninolytic genes in *Saccharomyces cerevisiae*," Bioengineered 2014;5:254-63.
Gonzalez-Perez D et al., "*Saccharomyces cerevisiae* in directed evolution: an efficient tool to improve enzymes," Bioengineered Bugs 2012;3:172-7.
Gonzalez-Perez D et al., "Structural determinants of oxidative stabilization in an evolved versatile peroxidase," ACS Catal. 2014;4:3891-901.
Gonzalez-Perez D et al., "The making of versatile peroxidase by directed evolution," Biocatal. Biotransform. 2017;36:1-11.
Janusz G et al., "Lignin degradation: microorganisms, enzymes involved, genomes analysis and evolution," FEMS Microbiol. Rev. 2017;41:941-62.
Kunamneni A et al., "Engineering and applications of fungal laccases for organic synthesis," Microbial Cell Factories 2008;7:32 (17 pp.).
Kunamneni A et al., "Laccases and their applications: a patent review," Recent Patents Biotechnol. 2008;2:10-24.
Li K et al., "Comparison of fungal laccases and redox mediators in oxidation of a nonphenolic lignin model compound," Appl. Environ. Microbiol. 1999;65:2654-60.
Lu Y et al., "Structural characterization of lignin and its degradation products with spectroscopic methods," J. Spectroscopy 2017; 8951658 (15 pp.).
Martínez Á, "High Redox Potential Peroxidases," Chapter 27 in Industrial Enzymes (J. Polaina and AP MacCabe, eds.), Springer (Dordrecht, the Netherlands), 2007, pp. 477-488.
Maté D et al., "Laboratory evolution of high-redox potential laccases," Chem. Biol. 2010;17:1030-41.
Mate DM et al., "Blood tolerant laccase by directed evolution," Chem. Biol. 2013;20:223-31.
Mate DM et al., "Laccase engineering: from rational design to directed evolution," Biotechnol. Adv. 2015;33:25-40.
Mate DM et al., "Laccase: a multi-purpose biocatalyst at the forefront of biotechnology," Microbial Biotechnol. 2017;10:1457-67.
Miller NJ et al., "Factors influencing the antioxidant activity determined by the ABTS•+ radical cation assay," Free Radic. Res. 1997;26:195-9.
Müller L et al., "Comparative antioxidant activities of carotenoids measured by ferric reducing antioxidant power (FRAP), ABTS bleaching assay (αTEAC), DPPH assay and peroxyl radical scavenging assay," Food Chem. 2011;129:139-48.

Munk L et al., "Can laccases catalyze bond cleavage in lignin?," Biotechnol. Adv. 2015;33:13-24.
Pardo I et al., "Development of chimeric laccases by directed evolution," Biotechnol. Bioeng. 2012;109:2978-86.
Phan TT et al., "Development of a strong intracellular expression system for Bacillus subtilis by optimizing promoter elements," J. Biotechnol. 2012;157(1):167-172.
Phan TT et al., "Development of Pgrac100-based expression vectors allowing high protein production levels in Bacillus subtilis and relatively low basal expression in *Escherichia coli*," Microb. Cell Fact. 2015;14:72 (9 pp.).
Pollegioni L et al., "Lignin-degrading enzymes," FEBS J. 2015;282:1190-213.
Re R et al., "Antioxidant activity applying an improved ABTS radical cation decolorization assay," Free Radic. Biol. Med. 1999;26:1231-7.
Tian XF et al., "Impact and prospective of fungal pre-treatment of lignocellulosic biomass for enzymatic hydrolysis," Biofuels Bioprod. Bioref. 2012;6:335-50.
Varman, Arul M., et al., "Decoding how a soil bacterium extracts building blocks and metabolic energy from ligninolysis provides road map for lignin valorization", Proceedings of the National Academy of Sciences, (Oct. 4, 2016), 113(40): E5802-E5811; first published Sep. 15, 2016 https://doi.org/10.1073/pnas.1606043113.
Varman, Arul Mohzy, et al., "Metabolic modeling and synthetic biology for the renewable production of fuels and chemicals", presentation poster, Sandia Report No. 2016-11725C; Conference: Proposed for presentation at the AICHE 2016 held Nov. 13-18, 2016 in San Francisco, CA, 1 page.
Varman, Arul Mohzy, et al., "S50: System and synthetic biology studies for effective lignin valorization", presented at the SIMB 2018, Annual Meeting and Exhibition held Aug. 13, 2018 in Chicago, IL, 1 page.
Varman, Arul Mohzy, et al., "Understanding and engineering microbial ligninolysis for chemical production", presentation poster, Sandia Report No. SAND2016-7679D; Conference: Proposed for presentation at the 2016 Biosciences External Advisory Board held Aug. 16-18, 2016 in Livermore, CA, 1 page.
Wang Y et al., "Plant cell wall lignification and monolignol metabolism," Front. Plant Sci. 2013;4:220 (14 pp.).
Wu, Weihua et al., "Lignin valorization: two hybrid biochemical routes for the conversion of polymeric lignin into value-added chemicals", Scientific Reports, (Aug. 21, 2017), vol. 7, Article No. 8420, 13 pages.
Wu, Weihua et al., "Toward engineering *E. coli* with an autoregulatory system for lignin valorization", Proceedings of the National Academy of Sciences, (Mar. 2018), 115(12): 2970-2975; DOI: 10.1073/pnas.1720129115.
UniProt Accession No. A0A067NKY1, "Peroxidase—VP3", 3 pages. [Retrieved from the Internet Apr. 3, 2020: <https://www.uniprot.org/uniprot/A0A067NKY1].
UniProt Accession No. A0A067NYV2, "Peroxidase—MnP4", 3 pages. [Retrieved from the Internet Apr. 3, 2020: <https://www.uniprot.org/uniprot/A0A067NYV2].
UniProt Accession No. A0A086DP91, "Uncharacterized protein—ETL41_02915", 2 pages. [Retrieved from the Internet Apr. 3, 2020: <https://www.uniprot.org/uniprot/A0A086DP91].
UniProt Accession No. A0A0A1MKV7, "Phosphoglycerate kinase, chloroplastic. D-amino acid dehydrogenase large subunit", 2 pages. [Retrieved from the Internet Apr. 3, 2020: <https://www.uniprot.org/uniprot/A0A0A1MKV7].
UniProt Accession No. A0A162R595, "Cell surface protein—B4417_2331", 1 page. [Retrieved from the Internet Apr. 3, 2020: <https://www.uniprot.org/uniprot/A0A162R595].
UniProt Accession No. A0A164SIA0, "Division initiation protein—B4417_3630", 1 page. [Retrieved from the Internet Apr. 3, 2020: <https://www.uniprot.org/uniprot/A0A164SIA0].
UniProt Accession No. A0A164SYK1, "Serine alkaline protease (Subtilisin E)—B4417_4207", 2 pages. [Retrieved from the Internet Apr. 3, 2020: <https://www.uniprot.org/uniprot/A0A164SYK1].
UniProt Accession No. A0A164VBM2, "D-amino acid dehydrogenase large subunit—B4417_1914", 1 page. [Retrieved from the Internet Apr. 3, 2020: <https://www.uniprot.org/uniprot/A0A164VBM2].

(56) References Cited

OTHER PUBLICATIONS

UniProt Accession No. A0A164VDT0, "YwsB—B4417_1998", 1 page. [Retrieved from the Internet Apr. 3, 2020: <https://www.uniprot.org/uniprot/A0A164VDT0].
UniProt Accession No. A0A164XYX0, "D-gamma-glutamyl-meso-diaminopimelic acid endopeptidase CwlS—B4417_0116", 2 pages. [Retrieved from the Internet Apr. 3, 2020: <https://www.uniprot.org/uniprot/A0A164XYX0].
UniProt Accession No. A0A1B2B3N6, "Uncharacterized protein—BH660_08470", 1 page. [Retrieved from the Internet Apr. 3, 2020: <https://www.uniprot.org/uniprot/A0A1B2B3N6].
UniProt Accession No. A0A1D8FNT7, "Uncharacterized protein—BH660_15970", 1 page. [Retrieved from the Internet Apr. 3, 2020: <https://www.uniprot.org/uniprot/A0A1D8FNT7].
UniProt Accession No. B2L9C1, "Laccase—Lac", 3 pages. [Retrieved from the Internet Apr. 3, 2020: <https://www.uniprot.org/uniprot/B2L9C1].
UniProt Accession No. C0KWE6, "Alpha-amylase—amyE", 2 pages. [Retrieved from the Internet Apr. 3, 2020: <https://www.uniprot.org/uniprot/C0KWE6].
UniProt Accession No. C0SPA3, "UPF0749 protein YlxW—ylxW", 2 pages. [Retrieved from the Internet Apr. 3, 2020: <https://www.uniprot.org/uniprot/C0SPA3].
UniProt Accession No. C7FH95, "Laccase—lcc1", 2 pages. [Retrieved from the Internet Apr. 3, 2020: <https://www.uniprot.org/uniprot/C7FH95].
UniProt Accession No. C9WKP8, "Laccase—lcc1", 2 pages. [Retrieved from the Internet Apr. 3, 2020: <https://www.uniprot.org/uniprot/C9WKP8].
UniProt Accession No. G4EY69, "Serine alkaline protease (Subtilisin E)—BSSC8_32990", 2 pages. [Retrieved from the Internet Mar. 23, 2020: <https://www.uniprot.org/uniprot/G4EY69].
UniProt Accession No. G4F096, "Alpha-amylase—BSSC8_40260", 2 pages. [Retrieved from the Internet Apr. 3, 2020: <https://www.uniprot.org/uniprot/G4F096].
UniProt Accession No. J0WUI3, "Peroxidase—GP11", 3 pages. [Retrieved from the Internet Apr. 3, 2020: <https://www.uniprot.org/uniprot/J0WUI3].
UniProt Accession No. L8AE42, Watanabe S., Shiwa Y., Itaya M., Yoshikawa H.; "Complete sequence of the first chimera genome constructed by cloning the whole genome of synechocystis strain PCC6803 into the Bacillus subtilis 168 genome", J. Bacteriol. 194:7007-7007(2012), 1 page. [Retrieved from the Internet Apr. 3, 2020: <https://www.uniprot.org/uniprot/L8AE42.txt?version=20].
UniProt Accession No. L8AEF2, Watanabe S., Shiwa Y., Itaya M., Yoshikawa H.; "Complete sequence of the first chimera genome constructed by cloning the whole genome of synechocystis strain PCC6803 into the Bacillus subtilis 168 genome", J. Bacteriol. 194:7007-7007(2012), 1 page. [Retrieved from the Internet Apr. 3, 2020: <https://www.uniprot.org/uniprot/L8AEF2].
UniProt Accession No. O31579, "Uncharacterized protein YfhK—yfhk", 2 pages. [Retrieved from the Internet Apr. 3, 2020: <https://www.uniprot.org/uniprot/O31579].
UniProt Accession No. O31852, "D-gamma-glutamyl-meso-diaminopimelic acid endopeptidase CwlS—cwlS", 3 pages. [Retrieved from the Internet Apr. 3, 2020: <https://www.uniprot.org/uniprot/O31852].
UniProt Accession No. O94753, "Versatile peroxidase VPL2—vpl2", 6 pages. [Retrieved from the Internet Apr. 3, 2020: <https://www.uniprot.org/uniprot/O94753].
UniProt Accession No. P00691, "Alpha-amylase—amyE", 6 pages. [Retrieved from the Internet Apr. 3, 2020: <https://www.uniprot.org/uniprot/P00691].
UniProt Accession No. P04189, "Subtilisin E—aprE", 6 pages. [Retrieved from the Internet Apr. 3, 2020: <https://www.uniprot.org/uniprot/P04189].
UniProt Accession No. P06181, "Ligninase H8—LPOA", 5 pages. [Retrieved from the Internet Apr. 3, 2020: <https://www.uniprot.org/uniprot/P06181].
UniProt Accession No. P42111, "Uncharacterized protein YxaL—yxaL", 3 pages. [Retrieved from the Internet Apr. 3, 2020: <https://www.uniprot.org/uniprot/P42111].
UniProt Accession No. P54172, "Uncharacterized protein YpjP—ypjP", 2 pages. [Retrieved from the Internet Apr. 3, 2020: <https://www.uniprot.org/uniprot/P54172].
UniProt Accession No. P68734, "Neutral protease NprE—nprE", 2 pages. [Retrieved from the Internet Apr. 3, 2020: <https://www.uniprot.org/uniprot/P68734].
UniProt Accession No. P68735, "Bacillolysin—nprE", 2 pages. [Retrieved from the Internet Apr. 3, 2020: <https://www.uniprot.org/uniprot/P68735].
UniProt Accession No. P68736, "Bacillolysin—nprE", 4 pages. [Retrieved from the Internet Apr. 3, 2020: <https://www.uniprot.org/uniprot/P68736].
UniProt Accession No. P70960, "Uncharacterized protein YwmC—ywmC", 2 pages. [Retrieved from the Internet Apr. 3, 2020: <https://www.uniprot.org/uniprot/P70960].
UniProt Accession No. P70961, "Uncharacterized protein YwmD—ywmD", 2 pages. [Retrieved from the Internet Apr. 3, 2020: <https://www.uniprot.org/uniprot/P70961].
UniProt Accession No. P96729, "Cell wall-binding protein YwsB—ywsB", 2 pages. [Retrieved from the Internet Apr. 3, 2020: <https://www.uniprot.org/uniprot/P96729].
UniProt Accession No. Q02567, "Manganese peroxidase 1—MNP1", 5 pages. [Retrieved from the Internet Apr. 3, 2020: <https://www.uniprot.org/uniprot/Q02567].
UniProt Accession No. Q12571, "Laccase", 3 pages. [Retrieved from the Internet Apr. 3, 2020: <https://www.uniprot.org/uniprot/Q12571].
UniProt Accession No. Q1W6B1, "Laccase—lac1", 3 pages. [Retrieved from the Internet Apr. 3, 2020: <https://www.uniprot.org/uniprot/Q1W6B1].
UniProt Accession No. Q2VT17, "Peroxidase—MnP5", 2 pages. [Retrieved from the Internet Apr. 3, 2020: <https://www.uniprot.org/uniprot/Q2VT17].
UniProt Accession No. Q53WT9, "Peroxidase—lgp3", 3 pages. [Retrieved from the Internet Apr. 3, 2020: <https://www.uniprot.org/uniprot/Q53WT9].
UniProt Accession No. Q5EBY5, "Laccase—lcc1", 3 pages. [Retrieved from the Internet Apr. 3, 2020: <https://www.uniprot.org/uniprot/Q5EBY5].
UniProt Accession No. Q5MBH6, "Laccase A—lacA", 2 pages. [Retrieved from the Internet Apr. 3, 2020: <https://www.uniprot.org/uniprot/Q5MBH6].
UniProt Accession No. Q70LM3, "Manganese peroxidase 2—mnp2", 3 pages. [Retrieved from the Internet Apr. 3, 2020: <https://www.uniprot.org/uniprot/Q70LM3].
UniProt Accession No. Q716A1, "Laccase—pox2", 2 pages. [Retrieved from the Internet Apr. 3, 2020: <https://www.uniprot.org/uniprot/Q716A1].
UniProt Accession No. Q8J1S4, "Peroxidase—vp13", 3 pages. [Retrieved from the Internet Apr. 3, 2020: <https://www.uniprot.org/uniprot/Q8J1S4].
UniProt Accession No. Q8TFM1, "Laccase III", 2 pages. [Retrieved from the Internet Apr. 3, 2020: <https://www.uniprot.org/uniprot/Q8TFM1].
UniProt Accession No. Q8TG94, "Laccase 2—lap2", 3 pages. [Retrieved from the Internet Apr. 3, 2020: <https://www.uniprot.org/uniprot/Q8TG94].
UniProt Accession No. Q96TR6, "Laccase—lcc1", 2 pages. [Retrieved from the Internet Apr. 3, 2020: <https://www.uniprot.org/uniprot/Q96TR6].
UniProt Accession No. Q9HDQ0, "Laccase—lcc1", 3 pages. [Retrieved from the Internet Apr. 3, 2020: <https://www.uniprot.org/uniprot/Q9HDQ0 ].
UniProt Accession No. Q9UR19, "Versatile peroxidase VPL1—vpl1 ", 4 pages. [Retrieved from the Internet Apr. 3, 2020: <https://www.uniprot.org/uniprot/Q9UR19].
UniProt Accession No. Q9UVP6, "Versatile peroxidase VPS1—vps1", 4 pages. [Retrieved from the Internet Apr. 3, 2020: <https://www.uniprot.org/uniprot/Q9UVP6].

(56) References Cited

OTHER PUBLICATIONS

UniProt Accession No. Q9UVQ2, "Laccase—lcc1", 3 pages. [Retrieved from the Internet Apr. 3, 2020: <https://www.uniprot.org/uniprot/Q9UVQ2>].

UniProt Accession No. Q9UVQ5, "Laccase 1—LAC1", 2 pages. [Retrieved from the Internet Apr. 3, 2020: <https://www.uniprot.org/uniprot/Q9UVQ5>].

UniProt Accession No. W8YE46, "Peroxidase—vpBad", 2 pages. [Retrieved from the Internet Apr. 3, 2020: <https://www.uniprot.org/uniprot/W8YE46>].

UniProt Accession No. W8YN06, "Peroxidase—LiPBad", 2 pages. [Retrieved from the Internet Apr. 3, 2020: <https://www.uniprot.org/uniprot/W8YN06>].

\* cited by examiner

Lac-1 (SEQ ID NO:1)
```
  1 SIGPVADLTI SNGAVSPDGF SRQAILVNDV FPSPLITGNK GDRFQLNVID NMTNHTMLKS
 61 TSIHWHGFFQ HGTNWADGPA FVNQCPISTG HAFLYDFQVP DQAGTFWYHS HLSTQYCDGL
121 RGPIVVYDPQ DPHKSLYDVD DDSTVITLAD WYHLAAKVGP AVPTADATLI NGLGRSIDTL
181 NADLAVITVT KGKRYRFRLV SLSCDPNHTF SIDGHSLTVI EADSVNLKPQ TVDSIQIFAA
241 QRYSFVLNAD QDVDNYWIRA LPNSGTRNFD GGVNSAILRY DGAAPVEPTT TQTPSTQPLV
301 ESALTTLEGT AAPGNPTPGG VDLALNMAFG FAGGRFTING ASFTPPTVPV LLQILSGAQS
361 AQDLLPSGSV YSLPANADIE ISLPATSAAP GFPHPFHLHG HTFAVVRSAG SSTYNYANPV
421 YRDVVSTGSP GDNVTIRFRT DNPGPWFLHC HIDFHLEAGF AVVMAEDIPE VAATNPVPQA
481 WSDLCPTYDA LSPDDQ
```

FIG. 1A

Lac-2 (SEQ ID NO:2)
```
  1 SIGPVADLTI SNGAVSPDGF SRQAILVNDV FPSPLITGNK GDRFQLNVID NMTNHTMLKS
 61 TSIHWHGFFQ HGTNWADGPA FVNQCPISTG HAFLYDFQVP DQAGTFWYHS HLSTQYCDGL
121 RGPIVVYDPQ DPHKSLYDVD DDSTVITLAD WYHLAAKVGP AAPTADATLI NGLGRSIDTL
181 NADLAVITVT KGKRYRFRLV SLSCDPNYTF SIDGHSLTVI EADGVNLKPQ TVDSIQIFPA
241 QRYSFVLNAD QDVDNYWIRA LPNSGTRNFD GGVNSAILRY EGAAPVEPTT TQTPSTQPLV
301 ESALTTLEGT AAPGNPTPGG VDLALNMAFG FAGGRFTING ASFTPPTVPV LLQILSGAQS
361 AQDLLPSGSV YSLPANADIE ISLPATSAAP GFPHPFHLHG HTFAVVRSAG SSTYNYANPV
421 YRDVVNTGSP GDNVTIRFRT DNPGPWFLHC HIDFHLEAGF TVVMAEDIPE VAATNPVPQA
481 WSDLCPTYDA LSPDDQ
```

FIG. 1B

Lac-3 (SEQ ID NO:3)
```
  1 SIGPVADLTI SNGAVSPDGF SRQAILVNDV FPSPLITGNK GDRFQLNVID NMTNHTMLKS
 61 TSIHWHGFFQ HGTNWADGPA FVNQCPISTG HAFLYDFQVP DQAGTFWYHS HLSTQYCDGL
121 RGPIVVYDPQ DPHKSLYDVD DDSTVITLAD WYHLAAKVGP AAPTADATLI NGLGRSIDTL
181 NADLAVITVT KGKRYRFRLV SLSCDPNYTF SIDGHSLTVI EADGVNLKPQ TVDSIQIFPA
241 QRYSFVLNAD QDVDNYWIRA LPNSGTRNFD GGVNSAILRY EGAAPVEPTT TQTPSTQPLV
301 ESALTTLEGT AAPGNPTPGG VDLALNMAFG FAGGRFTING ASFTPPTVPV LLQILSGAQS
361 AQDLLPSGSV YSLPANADIE ISLPATSAAP GFPHPIHLHG HTFAVVRSAG SSTYNYANPV
421 YRDVVNTGSP GDNVTIRFRT DNPGPWFLHC HIDEHLEAGF TVVMAEDIPE VAATNPVPQA
481 WSDLCPTYDA LSPDDQ
```

FIG. 1C

Lac-4 (SEQ ID NO:4)
```
  1 SIGPVADLTI SNGAVSPDGF SRQAILVNDV FPSPLITGNK GDRFQLNVID NMTNHTMLKS
 61 TSIHWHGFFQ HGTNWADGPA FVNQCPISTG HAFLYDFQVP DQAGTFWYHS HLSTQYCDGL
121 RGPIVVYDPQ DPHKSLYDVD DDSTVITLAD WYHLAAKVGP AVPTADATLI NGLGRSIDTL
181 NADLAVITVT KGKRYRFRLV SLSCDPNHTF SIDGHSLTVI EADSVNLKPQ TVDSIQIFAA
241 QRYSFVLNAD QDVDNYWIRA LPNSGTRNFD GGVNSAILRY DGAAPVEPTT TQTPSTQPLV
301 ESALTTLEGT AAPGNPTPGG VDLALNMAFG FAGGRFTING ASFTPPTVPV LLQILSGAQS
361 AQDLLPSGSV YSLPANADIE ISLPATSAAP GFPHPIHLHG HTFAVVRSAG SSTYNYANPV
421 YRDVVSTGSP GDNVTIRFRT DNPGPWFLHC HIDEHLEAGF AVVMAEDIPE VAATNPVPQA
481 WSDLCPTYDA LSPDDQ
```

FIG. 1D

```
Lac-10 (SEQ ID NO:10)
    1 AIGPVADLTL TNAQVSPDGF AREAVVVNGI TPAPLITGNK GDRFQLNVID QLTNHTMLKT
   61 SSIHWHGFFQ QGTNWADGPA FVNQCPIASG HSFLYDFQVP DQAGTFWYHS HLSTQYCDGL
  121 RGPFVVYDPN DPHASLYDID NDDTVITLAD WYHVAAKLGP RFPFGSDSTL INGLGRTTGI
  181 APSDLAVIKV TQGKRYRFRL VSLSCDPNHT FSIDNHTMTI IEADSINTQP LEVDSIQIFA
  241 AQRYSFVLDA SQPVDNYWIR ANPAFGNTGF AGGINSAILR YDGAPEIEPT SVQTTPTKPL
  301 NEVDLHPLSP MPVPGSPEPG GVDKPLNLVF NFNGTNFFIN DHTFVPPSVP VLLQILSGAQ
  361 AAQDLVPEGS VFVLPSNSSI EISFPATANA PGFPHPFHLH GHAFAVVRSA GSSVYNYDNP
  421 IFRDVVSTGQ PGDNVTIRFE TNNPGPWFLH CHIDFHLDAG FAVVMAEDTP DTKAANPVPQ
  481 AWSDLCPIYD ALDPSDL
```

FIG. 1E

```
Lac-11 (SEQ ID NO:11)
    1 AIGPVADLTL TNAQVSPDGF AREAVVVNGI TPAPLITGNK GDRFQLNVID QLTNHTMLKT
   61 SSIHWHGFFQ QGTNWADGPA FVNQCPIASG HSFLYDFQVP DQAGTFWYHS HLSTQYCDGL
  121 RGPFVVYDPN DPHASLYDID NDDTVITLAD WYHVAAKLGP RFPFGSDSTL INGLGRTTGI
  181 APSDLAVIKV TQGKRYRFRL VSLSCDPSHT FSIDNHTMTI IEADSINTQP LEVDSIQIFA
  241 AQRYSFVLDA SQPVDNYWIR ANPAFGNTGF AGGINSAILH YDGAPEIEPT SVQTTPTKPL
  301 NEVDLHPLSP MPVPGSPEPG GVDKPLNLVF DFNGTNFFIN NHTFVPPSVP VLLQILSGAQ
  361 AAQDLVPEGS VFVLPSNSSI EISFPATANA PGFHHPFHLH GHAFAVVRSA GSSVYNYDNP
  421 IFRDVVSTGQ PGDNVTIRFE TNNPGPWFLH CHIDFHLDAG FAVVMAEDTP DTKAANPVPQ
  481 AWSDLCPIYD ALDPSDL
```

FIG. 1F

```
VP-1 (SEQ ID NO:20)
    1 ATCDDGRTTA NAACCILFPI LDDIQENLFD GAQCGEEVHE SLRLTFHDAI GFSPTLGGGG
   61 ADGSIIAFDT IETNFPANAG IDEIVSAQKP FVAKHNISAG DFIQFAGAVG VSNCPGGVRI
  121 PFFLGRPDAV AASPDHLVPE PFDSVDSILA RMGDAGFSPV EVVWLLASHS IAAADKVDPS
  181 IPGTPFDSTP GVFDSQFFIE TQLKGRLFPG TADNKGEAQS PLQGEIRLQS DHLLARDPQT
  241 ACEWQSMVNN QPKIQNRFAA TMSKMALLGQ DKTKLIDCSD VIPTPPALVG AAHLPAGFSL
  301 SDVEQACAAT PFPALTADPG PVTSVPPVPG S
```

FIG. 2A

```
VP-2 (SEQ ID NO:21)
    1 ATCDDGRTTA NAACCILFPI LDDIQENLFD GAQCGEKVHE SLRLTFHDAI GFSPTLGGGG
   61 ADGSIIAFDT IETNFPANAG IDEIVSAQKP FVAKHNISAG DFIQFAGAVG VSNCPGGVRI
  121 PFFLGRPDAV AASPDHLVPE PFDSVDSILA RMGDAGFSPA EVVWLLASHS IAAADKVDPS
  181 IPGMPFDSTP GVFDSQFFIE TLLKGRLFPG TADNKGEAQS PLQGEIRLQS DHLLARDPQT
  241 ACEWQSMVNN QPKIQNRFAA TMSKMALLGQ DKTKLIDCSD VIPTPPALVG AAHLPAGFSL
  301 SDVEQACAAT PFPALTADPG PVTSVPPVPG S
```

FIG. 2B

VP-3 (SEQ ID NO:22)

```
  1 ATCDDGRTTA DAACCILFPI LDDIQENLFD GAQCKEKVHK SLRLAFHDAI GFSPTLGGGG
 61 ADGSIIAFDT IETNFPANAG IDEIVSAQEP FVAKHNISAG DFIQFAGAVG VSNCPGGVRI
121 PFFLGRPDAV AASPDHLVPE AFDSVDSILA RMGDAGFSPA EVVWLLASHS IAAADKVDPS
181 IPGMPLDSTP GVFDSQFFIE TLLKGRLFPG TADNKGEAQS PLQGEIRLQS DHLLARDPQT
241 ACEWQSMVNN QPKIQNRFAA TMSKMALLGQ DKTKLIDCSD VIPTPPALVG AAHLPAGFSL
301 SDVEQACAAT PFPALTADPG PVTSVPPVPG S
```

FIG. 2C

VP-4 (SEQ ID NO:23)

```
  1 ATCDDGRTTA NAACCILFPI LNDIQENLFD GAQCGEKVHE SLRLAFHDAI GFSPTLGGGG
 61 ADGSIIAFDT IETNFPANAG IDGIVSAQKP FVAKHNISAG DFVQFASAVG VSNCPGGVRI
121 PFFLGRPDAV AASPDHLVPE AFDSVDSILA RMGDAGFSPA EVVWLLASHS IAAADKVDPS
181 IPGMPLDSTP GVFDSQFFIE TLLKGRLFPG TADNKGEAQS PLQGEIRLQS DHLLARDPQT
241 ACEWQSMVNN QPKIQNRFAA TMSKMALLGQ DKTKLIDCSD VIPTPPALVG AAHLPAGFSL
301 SDVEQACAAT PFPALTADPG PVTSVPPVPG S
```

FIG. 2D

VP-5 (SEQ ID NO:24)

```
  1 ATCDDGRTTA DAACCILFPI LDDIQENLFD GAQCKEKVHK SLRLAFHDAI GFSPTLGGGG
 61 ADGSIIAFDT IETNFPANAG IDEIVRAQKP FVAKHNISAG DFIQFAGAVG VSNCPGGVRI
121 PFFLGRPDAV AASPDHLVPE AFDSVDSILA RMGDAGFSPA EVVWLLASHS IAAADKVDPS
181 IPGMPLDSTP GVFDSQFFIE TLLKGRLFPG TADNKGEAQS PLQGEIRLQS DHLLARDPQT
241 ACEWQSMVNN QPKIQNRFAA TMSKMALLGQ DKTKLIDCSD VIPTPPALVG AAHLPAGFSL
301 SDVEQACAAT PFPALTADPG PVISVPPVPG S
```

FIG. 2E

VP-6 (SEQ ID NO:25)

```
  1 ATCDDGRTTA NAACCILFPI LDDIQENLFD GAQCGEKVRE SLRLTFHDAI GFSPTLGGGG
 61 ADGSIIAFDT IETNFPANAG IDEIVSAQKP FVAKHNISAG DFIQFAGAVG VSNCPGGVRI
121 PFFLGRPDAV AASPDHLVPE PFDSVDSILA RMGDAGFSPA EVVWLLASHS IAAADKVDPS
181 IPGMPFDSTP GVFDSQFFIE TLLKGRLFPG TAANKGEAQS PLQGEIRLQS DHLLARDPQT
241 ACEWQSMVNN QPKIQNRFAA TMSKMALLGQ DKTKLIDCSD VIPTPPALVG AAHLPAGFSL
301 SDVEQACAAT PFPALTADPG PVTSVPPVPR S
```

FIG. 2F

SEQUENCE LISTING

```
<160> NUMBER OF SEQ ID NOS: 25

<210> SEQ ID NO 1
<211> LENGTH: 496
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(496)
<223> OTHER INFORMATION: optional mutations include, e.g., V162A, H208Y,
      S224G, A239P, D281E, S426N, A461T, D205N, F396I, S426D, I452V,
      F454E, F454P, F454T, F454A, F454G, F454R, T487S, N181D, A361T,
      V286L, P393H, P486L, F454S, S482L, and/or P486L

<400> SEQUENCE: 1

Ser Ile Gly Pro Val Ala Asp Leu Thr Ile Ser Asn Gly Ala Val Ser
1               5                   10                  15

Pro Asp Gly Phe Ser Arg Gln Ala Ile Leu Val Asn Asp Val Phe Pro
            20                  25                  30

Ser Pro Leu Ile Thr Gly Asn Lys Gly Asp Arg Phe Gln Leu Asn Val
        35                  40                  45

Ile Asp Asn Met Thr Asn His Thr Met Leu Lys Ser Thr Ser Ile His
    50                  55                  60

Trp His Gly Phe Phe Gln His Gly Thr Asn Trp Ala Asp Gly Pro Ala
65                  70                  75                  80

Phe Val Asn Gln Cys Pro Ile Ser Thr Gly His Ala Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Ile Val Val Tyr Asp
        115                 120                 125

Pro Gln Asp Pro His Lys Ser Leu Tyr Asp Val Asp Asp Asp Ser Thr
    130                 135                 140

Val Ile Thr Leu Ala Asp Trp Tyr His Leu Ala Ala Lys Val Gly Pro
145                 150                 155                 160
```

-continued

Ala Val Pro Thr Ala Asp Ala Thr Leu Ile Asn Gly Leu Gly Arg Ser
            165                 170                 175

Ile Asp Thr Leu Asn Ala Asp Leu Ala Val Ile Thr Val Thr Lys Gly
        180                 185                 190

Lys Arg Tyr Arg Phe Arg Leu Val Ser Leu Ser Cys Asp Pro Asn His
    195                 200                 205

Thr Phe Ser Ile Asp Gly His Ser Leu Thr Val Ile Glu Ala Asp Ser
210                 215                 220

Val Asn Leu Lys Pro Gln Thr Val Asp Ser Ile Gln Ile Phe Ala Ala
225                 230                 235                 240

Gln Arg Tyr Ser Phe Val Leu Asn Ala Asp Gln Asp Val Asp Asn Tyr
            245                 250                 255

Trp Ile Arg Ala Leu Pro Asn Ser Gly Thr Arg Asn Phe Asp Gly Gly
        260                 265                 270

Val Asn Ser Ala Ile Leu Arg Tyr Asp Gly Ala Ala Pro Val Glu Pro
    275                 280                 285

Thr Thr Thr Gln Thr Pro Ser Thr Gln Pro Leu Val Glu Ser Ala Leu
290                 295                 300

Thr Thr Leu Glu Gly Thr Ala Ala Pro Gly Asn Pro Thr Pro Gly Gly
305                 310                 315                 320

Val Asp Leu Ala Leu Asn Met Ala Phe Gly Phe Ala Gly Gly Arg Phe
            325                 330                 335

Thr Ile Asn Gly Ala Ser Phe Thr Pro Pro Thr Val Pro Val Leu Leu
        340                 345                 350

Gln Ile Leu Ser Gly Ala Gln Ser Ala Gln Asp Leu Leu Pro Ser Gly
    355                 360                 365

Ser Val Tyr Ser Leu Pro Ala Asn Ala Asp Ile Glu Ile Ser Leu Pro
370                 375                 380

Ala Thr Ser Ala Ala Pro Gly Phe Pro His Pro Phe His Leu His Gly
385                 390                 395                 400

His Thr Phe Ala Val Val Arg Ser Ala Gly Ser Ser Thr Tyr Asn Tyr
            405                 410                 415

Ala Asn Pro Val Tyr Arg Asp Val Val Ser Thr Gly Ser Pro Gly Asp
        420                 425                 430

Asn Val Thr Ile Arg Phe Arg Thr Asp Asn Pro Gly Pro Trp Phe Leu
    435                 440                 445

His Cys His Ile Asp Phe His Leu Glu Ala Gly Phe Ala Val Val Met
450                 455                 460

Ala Glu Asp Ile Pro Glu Val Ala Ala Thr Asn Pro Val Pro Gln Ala
465                 470                 475                 480

Trp Ser Asp Leu Cys Pro Thr Tyr Asp Ala Leu Ser Pro Asp Asp Gln
            485                 490                 495

<210> SEQ ID NO 2
<211> LENGTH: 496
<212> TYPE: PRT
<213> ORGANISM: Artificial Sequence
<220> FEATURE:
<223> OTHER INFORMATION: Synthetic construct

<400> SEQUENCE: 2

Ser Ile Gly Pro Val Ala Asp Leu Thr Ile Ser Asn Gly Ala Val Ser
1               5                   10                  15

Pro Asp Gly Phe Ser Arg Gln Ala Ile Leu Val Asn Asp Val Phe Pro
            20                  25                  30

```
Ser Pro Leu Ile Thr Gly Asn Lys Gly Asp Arg Phe Gln Leu Asn Val
         35                  40                  45

Ile Asp Asn Met Thr Asn His Thr Met Leu Lys Ser Thr Ser Ile His
 50                  55                  60

Trp His Gly Phe Phe Gln His Gly Thr Asn Trp Ala Asp Gly Pro Ala
 65                  70                  75                  80

Phe Val Asn Gln Cys Pro Ile Ser Thr Gly His Ala Phe Leu Tyr Asp
                 85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Ile Val Val Tyr Asp
            115                 120                 125

Pro Gln Asp Pro His Lys Ser Leu Tyr Asp Val Asp Asp Ser Thr
        130                 135                 140

Val Ile Thr Leu Ala Asp Trp Tyr His Leu Ala Ala Lys Val Gly Pro
145                 150                 155                 160

Ala Ala Pro Thr Ala Asp Ala Thr Leu Ile Asn Gly Leu Gly Arg Ser
                165                 170                 175

Ile Asp Thr Leu Asn Ala Asp Leu Ala Val Ile Thr Val Thr Lys Gly
                180                 185                 190

Lys Arg Tyr Arg Phe Arg Leu Val Ser Leu Ser Cys Asp Pro Asn Tyr
            195                 200                 205

Thr Phe Ser Ile Asp Gly His Ser Leu Thr Val Ile Glu Ala Asp Gly
            210                 215                 220

Val Asn Leu Lys Pro Gln Thr Val Asp Ser Ile Gln Ile Phe Pro Ala
225                 230                 235                 240

Gln Arg Tyr Ser Phe Val Leu Asn Ala Asp Gln Asp Val Asp Asn Tyr
                245                 250                 255

Trp Ile Arg Ala Leu Pro Asn Ser Gly Thr Arg Asn Phe Asp Gly Gly
                260                 265                 270

Val Asn Ser Ala Ile Leu Arg Tyr Glu Gly Ala Ala Pro Val Glu Pro
            275                 280                 285

Thr Thr Thr Gln Thr Pro Ser Thr Gln Pro Leu Val Glu Ser Ala Leu
            290                 295                 300

Thr Thr Leu Glu Gly Thr Ala Ala Pro Gly Asn Pro Thr Pro Gly Gly
305                 310                 315                 320

Val Asp Leu Ala Leu Asn Met Ala Phe Gly Phe Ala Gly Gly Arg Phe
                325                 330                 335

Thr Ile Asn Gly Ala Ser Phe Thr Pro Thr Val Pro Val Leu Leu
                340                 345                 350

Gln Ile Leu Ser Gly Ala Gln Ser Ala Gln Asp Leu Leu Pro Ser Gly
            355                 360                 365

Ser Val Tyr Ser Leu Pro Ala Asn Ala Asp Ile Glu Ile Ser Leu Pro
        370                 375                 380

Ala Thr Ser Ala Ala Pro Gly Phe Pro His Pro Phe His Leu His Gly
385                 390                 395                 400

His Thr Phe Ala Val Val Arg Ser Ala Gly Ser Ser Thr Tyr Asn Tyr
                405                 410                 415

Ala Asn Pro Val Tyr Arg Asp Val Val Asn Thr Gly Ser Pro Gly Asp
            420                 425                 430

Asn Val Thr Ile Arg Phe Arg Thr Asp Asn Pro Gly Pro Trp Phe Leu
            435                 440                 445

His Cys His Ile Asp Phe His Leu Glu Ala Gly Phe Thr Val Val Met
```

```
                    450                 455                 460
Ala Glu Asp Ile Pro Glu Val Ala Ala Thr Asn Pro Val Pro Gln Ala
465                 470                 475                 480

Trp Ser Asp Leu Cys Pro Thr Tyr Asp Ala Leu Ser Pro Asp Asp Gln
                    485                 490                 495

<210> SEQ ID NO 3
<211> LENGTH: 496
<212> TYPE: PRT
<213> ORGANISM: Artificial Sequence
<220> FEATURE:
<223> OTHER INFORMATION: Synthetic construct

<400> SEQUENCE: 3

Ser Ile Gly Pro Val Ala Asp Leu Thr Ile Ser Asn Gly Ala Val Ser
1               5                   10                  15

Pro Asp Gly Phe Ser Arg Gln Ala Ile Leu Val Asn Asp Val Phe Pro
                20                  25                  30

Ser Pro Leu Ile Thr Gly Asn Lys Gly Asp Arg Phe Gln Leu Asn Val
            35                  40                  45

Ile Asp Asn Met Thr Asn His Thr Met Leu Lys Ser Thr Ser Ile His
50                  55                  60

Trp His Gly Phe Phe Gln His Gly Thr Asn Trp Ala Asp Gly Pro Ala
65                  70                  75                  80

Phe Val Asn Gln Cys Pro Ile Ser Thr Gly His Ala Phe Leu Tyr Asp
                85                  90                  95

Phe Gln Val Pro Asp Gln Ala Gly Thr Phe Trp Tyr His Ser His Leu
                100                 105                 110

Ser Thr Gln Tyr Cys Asp Gly Leu Arg Gly Pro Ile Val Val Tyr Asp
            115                 120                 125

Pro Gln Asp Pro His Lys Ser Leu Tyr Asp Val Asp Asp Ser Thr
130                 135                 140

Val Ile Thr Leu Ala Asp Trp Tyr His Leu Ala Ala Lys Val Gly Pro
145                 150                 155                 160

Ala Ala Pro Thr Ala Asp Ala Thr Leu Ile Asn Gly Leu Gly Arg Ser
                165                 170                 175

Ile Asp Thr Leu Asn Ala Asp Leu Ala Val Ile Thr Val Thr Lys Gly
            180                 185                 190

Lys Arg Tyr Arg Phe Arg Leu Val Ser Leu Ser Cys Asp Pro Asn Tyr
                195                 200                 205

Thr Phe Ser Ile Asp Gly His Ser Leu Thr Val Ile Glu Ala Asp Gly
            210                 215                 220

Val Asn Leu Lys Pro Gln Thr Val Asp Ser Ile Gln Ile Phe Pro Ala
225                 230                 235                 240

Gln Arg Tyr Ser Phe Val Leu Asn Ala Asp Gln Asp Val Asp Asn Tyr
                245                 250                 255

Trp Ile Arg Ala Leu Pro Asn Ser Gly Thr Arg Asn Phe Asp Gly Gly
                260                 265                 270

Val Asn Ser Ala Ile Leu Arg Tyr Glu Gly Ala Ala Pro Val Glu Pro
            275                 280                 285

Thr Thr Thr Gln Thr Pro Ser Thr Gln Pro Leu Val Glu Ser Ala Leu
            290                 295                 300

Thr Thr Leu Glu Gly Thr Ala Ala Pro Gly Asn Pro Thr Pro Gly Gly
305                 310                 315                 320

Val Asp Leu Ala Leu Asn Met Ala Phe Gly Phe Ala Gly Gly Arg Phe
```

```
                    325                 330                 335
Thr Ile Asn Gly Ala Ser Phe Thr Pro Pro Thr Val Pro Val Leu Leu
                340                 345                 350

Gln Ile Leu Ser Gly Ala Gln Ser Ala Gln Asp Leu Leu Pro Ser Gly
            355                 360                 365

Ser Val Tyr Ser Leu Pro Ala Asn Ala Asp Ile Glu Ile Ser Leu Pro
        370                 375                 380

Ala Thr Ser Ala Ala Pro Gly Phe Pro His Pro Ile His Leu His Gly
385                 390                 395                 400

His Thr Phe Ala Val Val Arg Ser Ala Gly Ser Ser Thr Tyr Asn Tyr
                405                 410                 415

Ala Asn Pro Val Tyr Arg Asp Val Val Asn Thr Gly Ser Pro Gly Asp
                420                 425                 430

Asn Val Thr Ile Arg Phe Arg Thr Asp Asn Pro Gly Pro Trp Phe Leu
                435                 440                 445

His Cys His Ile Asp Glu His Leu Glu Ala Gly Phe Thr Val Val Met
                450                 455                 460

Ala Glu Asp Ile Pro Glu Val Ala Ala Thr Asn Pro Val Pro Gln Ala
465                 470                 475                 480

Trp Ser Asp Leu Cys Pro Thr Tyr Asp Ala Leu Ser Pro Asp Asp Gln
                485                 490                 495

<210> SEQ ID NO 4
<211> LENGTH: 496
<212> TYPE: PRT
<213> ORGANISM: Artificial Sequence
<220> FEATURE:
<223> OTHER INFORMATION: Synthetic construct

<400> SEQUENCE: 4

Ser Ile Gly Pro Val Ala Asp Leu Thr Ile Ser Asn Gly Ala Val Ser
1               5                   10                  15

Pro Asp Gly Phe Ser Arg Gln Ala Ile Leu Val Asn Asp Val Phe Pro
                20                  25                  30

Ser Pro Leu Ile Thr Gly Asn Lys Gly Asp Arg Phe Gln Leu Asn Val
            35                  40                  45

Ile Asp Asn Met Thr Asn His Thr Met Leu Lys Ser Thr Ile His
        50                  55                  60

Trp His Gly Phe Phe Gln His Gly Thr Asn Trp Ala Asp Gly Pro Ala
65                  70                  75                  80

Phe Val Asn Gln Cys Pro Ile Ser Thr Gly His Ala Phe Leu Tyr Asp
                85                  90                  95

Phe Gln Val Pro Asp Gln Ala Gly Thr Phe Trp Tyr His Ser His Leu
                100                 105                 110

Ser Thr Gln Tyr Cys Asp Gly Leu Arg Gly Pro Ile Val Val Tyr Asp
            115                 120                 125

Pro Gln Asp Pro His Lys Ser Leu Tyr Asp Val Asp Asp Ser Thr
        130                 135                 140

Val Ile Thr Leu Ala Asp Trp Tyr His Leu Ala Ala Lys Val Gly Pro
145                 150                 155                 160

Ala Val Pro Thr Ala Asp Ala Thr Leu Ile Asn Gly Leu Gly Arg Ser
                165                 170                 175

Ile Asp Thr Leu Asn Ala Asp Leu Ala Val Ile Thr Val Thr Lys Gly
                180                 185                 190

Lys Arg Tyr Arg Phe Arg Leu Val Ser Leu Ser Cys Asp Pro Asn His
```

-continued

```
                195                 200                 205
Thr Phe Ser Ile Asp Gly His Ser Leu Thr Val Ile Glu Ala Asp Ser
210                 215                 220
Val Asn Leu Lys Pro Gln Thr Val Asp Ser Ile Gln Ile Phe Ala Ala
225                 230                 235                 240
Gln Arg Tyr Ser Phe Val Leu Asn Ala Asp Gln Asp Val Asp Asn Tyr
                245                 250                 255
Trp Ile Arg Ala Leu Pro Asn Ser Gly Thr Arg Asn Phe Asp Gly Gly
                260                 265                 270
Val Asn Ser Ala Ile Leu Arg Tyr Asp Gly Ala Ala Pro Val Glu Pro
                275                 280                 285
Thr Thr Thr Gln Thr Pro Ser Thr Gln Pro Leu Val Glu Ser Ala Leu
290                 295                 300
Thr Thr Leu Glu Gly Thr Ala Ala Pro Gly Asn Pro Thr Pro Gly Gly
305                 310                 315                 320
Val Asp Leu Ala Leu Asn Met Ala Phe Gly Phe Ala Gly Gly Arg Phe
                325                 330                 335
Thr Ile Asn Gly Ala Ser Phe Thr Pro Pro Thr Val Pro Val Leu Leu
                340                 345                 350
Gln Ile Leu Ser Gly Ala Gln Ser Ala Gln Asp Leu Leu Pro Ser Gly
                355                 360                 365
Ser Val Tyr Ser Leu Pro Ala Asn Ala Asp Ile Glu Ile Ser Leu Pro
                370                 375                 380
Ala Thr Ser Ala Ala Pro Gly Phe Pro His Pro Ile His Leu His Gly
385                 390                 395                 400
His Thr Phe Ala Val Val Arg Ser Ala Gly Ser Ser Thr Tyr Asn Tyr
                405                 410                 415
Ala Asn Pro Val Tyr Arg Asp Val Val Ser Thr Gly Ser Pro Gly Asp
                420                 425                 430
Asn Val Thr Ile Arg Phe Arg Thr Asp Asn Pro Gly Pro Trp Phe Leu
                435                 440                 445
His Cys His Ile Asp Glu His Leu Glu Ala Gly Phe Ala Val Val Met
                450                 455                 460
Ala Glu Asp Ile Pro Glu Val Ala Ala Thr Asn Pro Val Pro Gln Ala
465                 470                 475                 480
Trp Ser Asp Leu Cys Pro Thr Tyr Asp Ala Leu Ser Pro Asp Asp Gln
                485                 490                 495
```

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 497
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(497)
<223> OTHER INFORMATION: optional mutations include, e.g., N208S, R280H,
    N331D, D341N, P394H, L46I, F81S, N130D, S135G, D255G, A240P,
    T294I, K324M, F332S, T428A, N443S, I453V, and/or D490G

<400> SEQUENCE: 10

```
Ala Ile Gly Pro Val Ala Asp Leu Thr Leu Thr Asn Ala Gln Val Ser
1               5                   10                  15

Pro Asp Gly Phe Ala Arg Glu Ala Val Val Asn Gly Ile Thr Pro
            20                  25                  30

Ala Pro Leu Ile Thr Gly Asn Lys Gly Asp Arg Phe Gln Leu Asn Val
        35                  40                  45

Ile Asp Gln Leu Thr Asn His Thr Met Leu Lys Thr Ser Ser Ile His
50                  55                  60

Trp His Gly Phe Gln Gln Gly Thr Asn Trp Ala Asp Gly Pro Ala
65                  70                  75                  80

Phe Val Asn Gln Cys Pro Ile Ala Ser Gly His Ser Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Phe Val Val Tyr Asp
        115                 120                 125

Pro Asn Asp Pro His Ala Ser Leu Tyr Asp Ile Asp Asn Asp Asp Thr
    130                 135                 140

Val Ile Thr Leu Ala Asp Trp Tyr His Val Ala Ala Lys Leu Gly Pro
145                 150                 155                 160

Arg Phe Pro Phe Gly Ser Asp Ser Thr Leu Ile Asn Gly Leu Gly Arg
                165                 170                 175

Thr Thr Gly Ile Ala Pro Ser Asp Leu Ala Val Ile Lys Val Thr Gln
            180                 185                 190

Gly Lys Arg Tyr Arg Phe Arg Leu Val Ser Leu Ser Cys Asp Pro Asn
        195                 200                 205

His Thr Phe Ser Ile Asp Asn His Thr Met Thr Ile Ile Glu Ala Asp
    210                 215                 220

Ser Ile Asn Thr Gln Pro Leu Glu Val Asp Ser Ile Gln Ile Phe Ala
225                 230                 235                 240

Ala Gln Arg Tyr Ser Phe Val Leu Asp Ala Ser Gln Pro Val Asp Asn
                245                 250                 255

Tyr Trp Ile Arg Ala Asn Pro Ala Phe Gly Asn Thr Gly Phe Ala Gly
            260                 265                 270
```

Gly Ile Asn Ser Ala Ile Leu Arg Tyr Asp Gly Ala Pro Glu Ile Glu
                275                 280                 285

Pro Thr Ser Val Gln Thr Thr Pro Thr Lys Pro Leu Asn Glu Val Asp
    290                 295                 300

Leu His Pro Leu Ser Pro Met Pro Val Pro Gly Ser Pro Glu Pro Gly
305                 310                 315                 320

Gly Val Asp Lys Pro Leu Asn Leu Val Phe Asn Phe Asn Gly Thr Asn
                325                 330                 335

Phe Phe Ile Asn Asp His Thr Phe Val Pro Pro Ser Val Pro Val Leu
                340                 345                 350

Leu Gln Ile Leu Ser Gly Ala Gln Ala Ala Gln Asp Leu Val Pro Glu
            355                 360                 365

Gly Ser Val Phe Val Leu Pro Ser Asn Ser Ser Ile Glu Ile Ser Phe
        370                 375                 380

Pro Ala Thr Ala Asn Ala Pro Gly Phe Pro His Pro Phe His Leu His
385                 390                 395                 400

Gly His Ala Phe Ala Val Val Arg Ser Ala Gly Ser Ser Val Tyr Asn
                405                 410                 415

Tyr Asp Asn Pro Ile Phe Arg Asp Val Val Ser Thr Gly Gln Pro Gly
            420                 425                 430

Asp Asn Val Thr Ile Arg Phe Glu Thr Asn Asn Pro Gly Pro Trp Phe
        435                 440                 445

Leu His Cys His Ile Asp Phe His Leu Asp Ala Gly Phe Ala Val Val
    450                 455                 460

Met Ala Glu Asp Thr Pro Asp Thr Lys Ala Ala Asn Pro Val Pro Gln
465                 470                 475                 480

Ala Trp Ser Asp Leu Cys Pro Ile Tyr Asp Ala Leu Asp Pro Ser Asp
                485                 490                 495

Leu

<210> SEQ ID NO 11
<211> LENGTH: 497
<212> TYPE: PRT
<213> ORGANISM: Artificial Sequence
<220> FEATURE:
<223> OTHER INFORMATION: Synthetic construct

<400> SEQUENCE: 11

Ala Ile Gly Pro Val Ala Asp Leu Thr Leu Thr Asn Ala Gln Val Ser
1               5                   10                  15

Pro Asp Gly Phe Ala Arg Glu Ala Val Val Asn Gly Ile Thr Pro
            20                  25                  30

Ala Pro Leu Ile Thr Gly Asn Lys Gly Asp Arg Phe Gln Leu Asn Val
            35                  40                  45

Ile Asp Gln Leu Thr Asn His Thr Met Leu Lys Thr Ser Ser Ile His
    50                  55                  60

Trp His Gly Phe Phe Gln Gln Gly Thr Asn Trp Ala Asp Gly Pro Ala
65                  70                  75                  80

Phe Val Asn Gln Cys Pro Ile Ala Ser Gly His Ser Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Phe Val Val Tyr Asp
        115                 120                 125

Pro Asn Asp Pro His Ala Ser Leu Tyr Asp Ile Asp Asn Asp Asp Thr

```
              130                 135                 140
Val Ile Thr Leu Ala Asp Trp Tyr His Val Ala Lys Leu Gly Pro
145                 150                 155                 160

Arg Phe Pro Phe Gly Ser Asp Ser Thr Leu Ile Asn Gly Leu Gly Arg
                165                 170                 175

Thr Thr Gly Ile Ala Pro Ser Asp Leu Ala Val Ile Lys Val Thr Gln
                180                 185                 190

Gly Lys Arg Tyr Arg Phe Arg Leu Val Ser Leu Ser Cys Asp Pro Ser
                195                 200                 205

His Thr Phe Ser Ile Asp Asn His Thr Met Thr Ile Ile Glu Ala Asp
                210                 215                 220

Ser Ile Asn Thr Gln Pro Leu Glu Val Asp Ser Ile Gln Ile Phe Ala
225                 230                 235                 240

Ala Gln Arg Tyr Ser Phe Val Leu Asp Ala Ser Gln Pro Val Asp Asn
                245                 250                 255

Tyr Trp Ile Arg Ala Asn Pro Ala Phe Gly Asn Thr Gly Phe Ala Gly
                260                 265                 270

Gly Ile Asn Ser Ala Ile Leu His Tyr Asp Gly Ala Pro Glu Ile Glu
                275                 280                 285

Pro Thr Ser Val Gln Thr Thr Pro Thr Lys Pro Leu Asn Glu Val Asp
                290                 295                 300

Leu His Pro Leu Ser Pro Met Pro Val Pro Gly Ser Pro Glu Pro Gly
305                 310                 315                 320

Gly Val Asp Lys Pro Leu Asn Leu Val Phe Asp Phe Asn Gly Thr Asn
                325                 330                 335

Phe Phe Ile Asn Asn His Thr Phe Val Pro Pro Ser Val Pro Val Leu
                340                 345                 350

Leu Gln Ile Leu Ser Gly Ala Gln Ala Ala Gln Asp Leu Val Pro Glu
                355                 360                 365

Gly Ser Val Phe Val Leu Pro Ser Asn Ser Ser Ile Glu Ile Ser Phe
                370                 375                 380

Pro Ala Thr Ala Asn Ala Pro Gly Phe His His Pro Phe His Leu His
385                 390                 395                 400

Gly His Ala Phe Ala Val Val Arg Ser Ala Gly Ser Ser Val Tyr Asn
                405                 410                 415

Tyr Asp Asn Pro Ile Phe Arg Asp Val Val Ser Thr Gly Gln Pro Gly
                420                 425                 430

Asp Asn Val Thr Ile Arg Phe Glu Thr Asn Asn Pro Gly Pro Trp Phe
                435                 440                 445

Leu His Cys His Ile Asp Phe His Leu Asp Ala Gly Phe Ala Val Val
                450                 455                 460

Met Ala Glu Asp Thr Pro Asp Thr Lys Ala Ala Asn Pro Val Pro Gln
465                 470                 475                 480

Ala Trp Ser Asp Leu Cys Pro Ile Tyr Asp Ala Leu Asp Pro Ser Asp
                485                 490                 495

Leu

<210> SEQ ID NO 12

<400> SEQUENCE: 12

000

<210> SEQ ID NO 13
```

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 331
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(331)
<223> OTHER INFORMATION: optional mutations include, e.g., E37K, V160A,
    T184M, Q202L,H39R, D213A, and/or G330R
<220> FEATURE:
<221> NAME/KEY: MISC_FEATURE
<222> LOCATION: (1)..(331)
<223> OTHER INFORMATION: optional mutations include, e.g., N11D, D22N,
    G35K, H39R, E40K, T45A, D82G, E83K, E83G, E83S, E83V, S86R, K89E,
    K89M, I103V, G107S, E140G, P141A, P182S, P182H, G183E, T184D,
    T184S, F186L, D213A, N214Y, Q219R, Q229P, T323I, and/or G330R

<400> SEQUENCE: 20

Ala Thr Cys Asp Asp Gly Arg Thr Thr Ala Asn Ala Ala Cys Cys Ile
1               5                   10                  15

Leu Phe Pro Ile Leu Asp Asp Ile Gln Glu Asn Leu Phe Asp Gly Ala
                20                  25                  30

Gln Cys Gly Glu Glu Val His Glu Ser Leu Arg Leu Thr Phe His Asp
            35                  40                  45

Ala Ile Gly Phe Ser Pro Thr Leu Gly Gly Gly Gly Ala Asp Gly Ser

```
        50                  55                  60
Ile Ile Ala Phe Asp Thr Ile Glu Thr Asn Phe Pro Ala Asn Ala Gly
 65                  70                  75                  80

Ile Asp Glu Ile Val Ser Ala Gln Lys Pro Phe Val Ala Lys His Asn
                 85                  90                  95

Ile Ser Ala Gly Asp Phe Ile Gln Phe Ala Gly Ala Val Gly Val Ser
                100                 105                 110

Asn Cys Pro Gly Gly Val Arg Ile Pro Phe Phe Leu Gly Arg Pro Asp
                115                 120                 125

Ala Val Ala Ala Ser Pro Asp His Leu Val Pro Glu Pro Phe Asp Ser
            130                 135                 140

Val Asp Ser Ile Leu Ala Arg Met Gly Asp Ala Gly Phe Ser Pro Val
145                 150                 155                 160

Glu Val Val Trp Leu Leu Ala Ser His Ser Ile Ala Ala Ala Asp Lys
                165                 170                 175

Val Asp Pro Ser Ile Pro Gly Thr Pro Phe Asp Ser Thr Pro Gly Val
                180                 185                 190

Phe Asp Ser Gln Phe Phe Ile Glu Thr Gln Leu Lys Gly Arg Leu Phe
            195                 200                 205

Pro Gly Thr Ala Asp Asn Lys Gly Glu Ala Gln Ser Pro Leu Gln Gly
210                 215                 220

Glu Ile Arg Leu Gln Ser Asp His Leu Leu Ala Arg Asp Pro Gln Thr
225                 230                 235                 240

Ala Cys Glu Trp Gln Ser Met Val Asn Asn Gln Pro Lys Ile Gln Asn
                245                 250                 255

Arg Phe Ala Ala Thr Met Ser Lys Met Ala Leu Leu Gly Gln Asp Lys
                260                 265                 270

Thr Lys Leu Ile Asp Cys Ser Asp Val Ile Pro Thr Pro Pro Ala Leu
                275                 280                 285

Val Gly Ala Ala His Leu Pro Ala Gly Phe Ser Leu Ser Asp Val Glu
            290                 295                 300

Gln Ala Cys Ala Ala Thr Pro Phe Pro Ala Leu Thr Ala Asp Pro Gly
305                 310                 315                 320

Pro Val Thr Ser Val Pro Pro Val Pro Gly Ser
                325                 330

<210> SEQ ID NO 21
<211> LENGTH: 331
<212> TYPE: PRT
<213> ORGANISM: Artificial Sequence
<220> FEATURE:
<223> OTHER INFORMATION: Synthetic construct

<400> SEQUENCE: 21

Ala Thr Cys Asp Asp Gly Arg Thr Thr Ala Asn Ala Ala Cys Cys Ile
 1               5                  10                  15

Leu Phe Pro Ile Leu Asp Asp Ile Gln Glu Asn Leu Phe Asp Gly Ala
                20                  25                  30

Gln Cys Gly Glu Lys Val His Glu Ser Leu Arg Leu Thr Phe His Asp
            35                  40                  45

Ala Ile Gly Phe Ser Pro Thr Leu Gly Gly Gly Ala Asp Gly Ser
            50                  55                  60

Ile Ile Ala Phe Asp Thr Ile Glu Thr Asn Phe Pro Ala Asn Ala Gly
 65                  70                  75                  80

Ile Asp Glu Ile Val Ser Ala Gln Lys Pro Phe Val Ala Lys His Asn
```

```
                    85                  90                  95
Ile Ser Ala Gly Asp Phe Ile Gln Phe Ala Gly Ala Val Gly Val Ser
                100                 105                 110
Asn Cys Pro Gly Gly Val Arg Ile Pro Phe Phe Leu Gly Arg Pro Asp
                115                 120                 125
Ala Val Ala Ala Ser Pro Asp His Leu Val Pro Glu Pro Phe Asp Ser
            130                 135                 140
Val Asp Ser Ile Leu Ala Arg Met Gly Asp Ala Gly Phe Ser Pro Ala
145                 150                 155                 160
Glu Val Val Trp Leu Leu Ala Ser His Ser Ile Ala Ala Asp Lys
                165                 170                 175
Val Asp Pro Ser Ile Pro Gly Met Pro Phe Asp Ser Thr Pro Gly Val
            180                 185                 190
Phe Asp Ser Gln Phe Phe Ile Glu Thr Leu Leu Lys Gly Arg Leu Phe
        195                 200                 205
Pro Gly Thr Ala Asp Asn Lys Gly Glu Ala Gln Ser Pro Leu Gln Gly
        210                 215                 220
Glu Ile Arg Leu Gln Ser Asp His Leu Leu Ala Arg Asp Pro Gln Thr
225                 230                 235                 240
Ala Cys Glu Trp Gln Ser Met Val Asn Asn Gln Pro Lys Ile Gln Asn
                245                 250                 255
Arg Phe Ala Ala Thr Met Ser Lys Met Ala Leu Leu Gly Gln Asp Lys
            260                 265                 270
Thr Lys Leu Ile Asp Cys Ser Asp Val Ile Pro Thr Pro Pro Ala Leu
        275                 280                 285
Val Gly Ala Ala His Leu Pro Ala Gly Phe Ser Leu Ser Asp Val Glu
        290                 295                 300
Gln Ala Cys Ala Ala Thr Pro Phe Pro Ala Leu Thr Ala Asp Pro Gly
305                 310                 315                 320
Pro Val Thr Ser Val Pro Pro Val Pro Gly Ser
                325                 330

<210> SEQ ID NO 22
<211> LENGTH: 331
<212> TYPE: PRT
<213> ORGANISM: Artificial Sequence
<220> FEATURE:
<223> OTHER INFORMATION: Synthetic construct

<400> SEQUENCE: 22

Ala Thr Cys Asp Asp Gly Arg Thr Thr Ala Asp Ala Ala Cys Cys Ile
1               5                   10                  15
Leu Phe Pro Ile Leu Asp Asp Ile Gln Glu Asn Leu Phe Asp Gly Ala
                20                  25                  30
Gln Cys Lys Glu Lys Val His Lys Ser Leu Arg Leu Ala Phe His Asp
            35                  40                  45
Ala Ile Gly Phe Ser Pro Thr Leu Gly Gly Gly Ala Asp Gly Ser
        50                  55                  60
Ile Ile Ala Phe Asp Thr Ile Glu Thr Asn Phe Pro Ala Asn Ala Gly
65                  70                  75                  80
Ile Asp Glu Ile Val Ser Ala Gln Glu Pro Phe Val Ala Lys His Asn
                85                  90                  95
Ile Ser Ala Gly Asp Phe Ile Gln Phe Ala Gly Ala Val Gly Val Ser
                100                 105                 110
Asn Cys Pro Gly Gly Val Arg Ile Pro Phe Phe Leu Gly Arg Pro Asp
```

```
            115                 120                 125
Ala Val Ala Ala Ser Pro Asp His Leu Val Pro Glu Ala Phe Asp Ser
        130                 135                 140

Val Asp Ser Ile Leu Ala Arg Met Gly Asp Ala Gly Phe Ser Pro Ala
145                 150                 155                 160

Glu Val Val Trp Leu Leu Ala Ser His Ser Ile Ala Ala Asp Lys
                165                 170                 175

Val Asp Pro Ser Ile Pro Gly Met Pro Leu Asp Ser Thr Pro Gly Val
            180                 185                 190

Phe Asp Ser Gln Phe Phe Ile Glu Thr Leu Leu Lys Gly Arg Leu Phe
        195                 200                 205

Pro Gly Thr Ala Asp Asn Lys Gly Glu Ala Gln Ser Pro Leu Gln Gly
    210                 215                 220

Glu Ile Arg Leu Gln Ser Asp His Leu Leu Ala Arg Asp Pro Gln Thr
225                 230                 235                 240

Ala Cys Glu Trp Gln Ser Met Val Asn Asn Gln Pro Lys Ile Gln Asn
                245                 250                 255

Arg Phe Ala Ala Thr Met Ser Lys Met Ala Leu Leu Gly Gln Asp Lys
            260                 265                 270

Thr Lys Leu Ile Asp Cys Ser Asp Val Ile Pro Thr Pro Pro Ala Leu
        275                 280                 285

Val Gly Ala Ala His Leu Pro Ala Gly Phe Ser Leu Ser Asp Val Glu
    290                 295                 300

Gln Ala Cys Ala Ala Thr Pro Phe Pro Ala Leu Thr Ala Asp Pro Gly
305                 310                 315                 320

Pro Val Thr Ser Val Pro Pro Val Pro Gly Ser
                325                 330

<210> SEQ ID NO 23
<211> LENGTH: 331
<212> TYPE: PRT
<213> ORGANISM: Artificial Sequence
<220> FEATURE:
<223> OTHER INFORMATION: Synthetic construct

<400> SEQUENCE: 23

Ala Thr Cys Asp Asp Gly Arg Thr Thr Ala Asn Ala Ala Cys Cys Ile
1               5                   10                  15

Leu Phe Pro Ile Leu Asn Asp Ile Gln Glu Asn Leu Phe Asp Gly Ala
                20                  25                  30

Gln Cys Gly Glu Lys Val His Glu Ser Leu Arg Leu Ala Phe His Asp
            35                  40                  45

Ala Ile Gly Phe Ser Pro Thr Leu Gly Gly Gly Ala Asp Gly Ser
        50                  55                  60

Ile Ile Ala Phe Asp Thr Ile Glu Thr Asn Phe Pro Ala Asn Ala Gly
65                  70                  75                  80

Ile Asp Gly Ile Val Ser Ala Gln Lys Pro Phe Val Ala Lys His Asn
                85                  90                  95

Ile Ser Ala Gly Asp Phe Val Gln Phe Ala Ser Ala Val Gly Val Ser
            100                 105                 110

Asn Cys Pro Gly Gly Val Arg Ile Pro Phe Phe Leu Gly Arg Pro Asp
        115                 120                 125

Ala Val Ala Ala Ser Pro Asp His Leu Val Pro Glu Ala Phe Asp Ser
    130                 135                 140

Val Asp Ser Ile Leu Ala Arg Met Gly Asp Ala Gly Phe Ser Pro Ala
```

```
145                 150                 155                 160
Glu Val Val Trp Leu Leu Ala Ser His Ser Ile Ala Ala Asp Lys
                165                 170                 175

Val Asp Pro Ser Ile Pro Gly Met Pro Leu Asp Ser Thr Pro Gly Val
            180                 185                 190

Phe Asp Ser Gln Phe Phe Ile Glu Thr Leu Leu Lys Gly Arg Leu Phe
        195                 200                 205

Pro Gly Thr Ala Asp Asn Lys Gly Glu Ala Gln Ser Pro Leu Gln Gly
    210                 215                 220

Glu Ile Arg Leu Gln Ser Asp His Leu Leu Ala Arg Asp Pro Gln Thr
225                 230                 235                 240

Ala Cys Glu Trp Gln Ser Met Val Asn Asn Gln Pro Lys Ile Gln Asn
                245                 250                 255

Arg Phe Ala Ala Thr Met Ser Lys Met Ala Leu Leu Gly Gln Asp Lys
            260                 265                 270

Thr Lys Leu Ile Asp Cys Ser Asp Val Ile Pro Thr Pro Pro Ala Leu
        275                 280                 285

Val Gly Ala Ala His Leu Pro Ala Gly Phe Ser Leu Ser Asp Val Glu
    290                 295                 300

Gln Ala Cys Ala Ala Thr Pro Phe Pro Ala Leu Thr Ala Asp Pro Gly
305                 310                 315                 320

Pro Val Thr Ser Val Pro Pro Val Pro Gly Ser
                325                 330

<210> SEQ ID NO 24
<211> LENGTH: 331
<212> TYPE: PRT
<213> ORGANISM: Artificial Sequence
<220> FEATURE:
<223> OTHER INFORMATION: Synthetic construct

<400> SEQUENCE: 24

Ala Thr Cys Asp Asp Gly Arg Thr Thr Ala Asp Ala Ala Cys Cys Ile
1               5                   10                  15

Leu Phe Pro Ile Leu Asp Asp Ile Gln Glu Asn Leu Phe Asp Gly Ala
            20                  25                  30

Gln Cys Lys Glu Lys Val His Lys Ser Leu Arg Leu Ala Phe His Asp
        35                  40                  45

Ala Ile Gly Phe Ser Pro Thr Leu Gly Gly Gly Ala Asp Gly Ser
    50                  55                  60

Ile Ile Ala Phe Asp Thr Ile Glu Thr Asn Phe Pro Ala Asn Ala Gly
65                  70                  75                  80

Ile Asp Glu Ile Val Arg Ala Gln Lys Pro Phe Val Ala Lys His Asn
                85                  90                  95

Ile Ser Ala Gly Asp Phe Ile Gln Phe Ala Gly Ala Val Gly Val Ser
            100                 105                 110

Asn Cys Pro Gly Gly Val Arg Ile Pro Phe Phe Leu Gly Arg Pro Asp
        115                 120                 125

Ala Val Ala Ala Ser Pro Asp His Leu Val Pro Glu Ala Phe Asp Ser
    130                 135                 140

Val Asp Ser Ile Leu Ala Arg Met Gly Asp Ala Gly Phe Ser Pro Ala
145                 150                 155                 160

Glu Val Val Trp Leu Leu Ala Ser His Ser Ile Ala Ala Ala Asp Lys
                165                 170                 175

Val Asp Pro Ser Ile Pro Gly Met Pro Leu Asp Ser Thr Pro Gly Val
```

```
            180                 185                 190
Phe Asp Ser Gln Phe Phe Ile Glu Thr Leu Leu Lys Gly Arg Leu Phe
            195                 200                 205
Pro Gly Thr Ala Asp Asn Lys Gly Glu Ala Gln Ser Pro Leu Gln Gly
        210                 215                 220
Glu Ile Arg Leu Gln Ser Asp His Leu Leu Ala Arg Asp Pro Gln Thr
225                 230                 235                 240
Ala Cys Glu Trp Gln Ser Met Val Asn Asn Gln Pro Lys Ile Gln Asn
                245                 250                 255
Arg Phe Ala Ala Thr Met Ser Lys Met Ala Leu Leu Gly Gln Asp Lys
            260                 265                 270
Thr Lys Leu Ile Asp Cys Ser Asp Val Ile Pro Thr Pro Pro Ala Leu
        275                 280                 285
Val Gly Ala Ala His Leu Pro Ala Gly Phe Ser Leu Ser Asp Val Glu
    290                 295                 300
Gln Ala Cys Ala Ala Thr Pro Phe Pro Ala Leu Thr Ala Asp Pro Gly
305                 310                 315                 320
Pro Val Ile Ser Val Pro Pro Val Pro Gly Ser
                325                 330

<210> SEQ ID NO 25
<211> LENGTH: 331
<212> TYPE: PRT
<213> ORGANISM: Artificial Sequence
<220> FEATURE:
<223> OTHER INFORMATION: Synthetic construct

<400> SEQUENCE: 25

Ala Thr Cys Asp Asp Gly Arg Thr Thr Ala Asn Ala Ala Cys Cys Ile
1               5                   10                  15
Leu Phe Pro Ile Leu Asp Asp Ile Gln Glu Asn Leu Phe Asp Gly Ala
            20                  25                  30
Gln Cys Gly Glu Lys Val Arg Glu Ser Leu Arg Leu Thr Phe His Asp
        35                  40                  45
Ala Ile Gly Phe Ser Pro Thr Leu Gly Gly Gly Gly Ala Asp Gly Ser
    50                  55                  60
Ile Ile Ala Phe Asp Thr Ile Glu Thr Asn Phe Pro Ala Asn Ala Gly
65                  70                  75                  80
Ile Asp Glu Ile Val Ser Ala Gln Lys Pro Phe Val Ala Lys His Asn
                85                  90                  95
Ile Ser Ala Gly Asp Phe Ile Gln Phe Ala Gly Ala Val Gly Val Ser
            100                 105                 110
Asn Cys Pro Gly Gly Val Arg Ile Pro Phe Phe Leu Gly Arg Pro Asp
        115                 120                 125
Ala Val Ala Ala Ser Pro Asp His Leu Val Pro Glu Pro Phe Asp Ser
    130                 135                 140
Val Asp Ser Ile Leu Ala Arg Met Gly Asp Ala Gly Phe Ser Pro Ala
145                 150                 155                 160
Glu Val Val Trp Leu Leu Ala Ser His Ser Ile Ala Ala Ala Asp Lys
                165                 170                 175
Val Asp Pro Ser Ile Pro Gly Met Pro Phe Asp Ser Thr Pro Gly Val
            180                 185                 190
Phe Asp Ser Gln Phe Phe Ile Glu Thr Leu Leu Lys Gly Arg Leu Phe
        195                 200                 205
Pro Gly Thr Ala Ala Asn Lys Gly Glu Ala Gln Ser Pro Leu Gln Gly
```

-continued

```
            210                 215                 220
Glu Ile Arg Leu Gln Ser Asp His Leu Leu Ala Arg Asp Pro Gln Thr
225                 230                 235                 240

Ala Cys Glu Trp Gln Ser Met Val Asn Asn Gln Pro Lys Ile Gln Asn
                245                 250                 255

Arg Phe Ala Ala Thr Met Ser Lys Met Ala Leu Leu Gly Gln Asp Lys
                260                 265                 270

Thr Lys Leu Ile Asp Cys Ser Asp Val Ile Pro Thr Pro Pro Ala Leu
                275                 280                 285

Val Gly Ala Ala His Leu Pro Ala Gly Phe Ser Leu Ser Asp Val Glu
                290                 295                 300

Gln Ala Cys Ala Ala Thr Pro Phe Pro Ala Leu Thr Ala Asp Pro Gly
305                 310                 315                 320

Pro Val Thr Ser Val Pro Pro Val Pro Arg Ser
                325                 330
```

ENGINEERED HOSTS WITH EXOGENOUS LIGNINASE AND USES THEREOF

CROSS-REFERENCE TO RELATED APPLICATION

This application claims the benefit of U.S. Provisional Application No. 62/829,182, filed Apr. 4, 2019, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named SANDP001_sequence_listing_3_ST25.txt, created on May 29, 2020 (size of 45 kilobytes), which is hereby incorporated by reference in its entirety.

FIELD OF THE INVENTION

The present invention relates to methods and engineered microbial hosts useful for treating lignin or a derivative thereof. In some embodiments, the host has one or more exogenous nucleic acid sequences that encode a ligninase (e.g., a laccase and/or a peroxidase).

BACKGROUND OF THE INVENTION

Lignin is a renewable resource that requires depolymerization to release high value chemical intermediates. Depolymerizing can include cleavage of various functional groups, including aryl linkages and carbon-carbon bonds. Bacterial catabolism is one approach to decompose lignin and its derivatives, yet additional improvements to efficient and controlled depolymerization are desired.

SUMMARY OF THE INVENTION

The present invention relates to methods and engineered hosts to depolymerize lignin with secreted fungal ligninases. In particular, we describe an exemplary engineered host that secrete one or more fungal enzymes that degrade lignin. Methods of using such hosts to treat lignin are also described herein.

Accordingly, in a first aspect, the present invention features a method (e.g., of treating lignin or a derivative thereof) including: providing an engineered microbial host including one or more exogenous nucleic acid sequences, where at least one exogenous nucleic acid sequence encodes a laccase and/or a peroxidase; and introducing the engineered microbial source to a source including lignin or a derivative thereof at a pH of from about 3 to about 6 (e.g., of from about 4 to 6, 5 to 6, or 5.2 to 5.7).

In some embodiments, the at least one exogenous nucleic acid sequence encodes the laccase (e.g., a high-redox potential laccase, such as any described herein) and the peroxidase (e.g., a versatile peroxidase, such as any described herein).

In some embodiments, the at least one exogenous nucleic acid sequence encodes the laccase and/or the peroxidase in a sequence that is codon-optimized for the host.

In some embodiments, the laccase and/or the peroxidase is derived from a fungus. In other embodiments, the laccase includes an amino acid sequence having at least 80% sequence identity to one of SEQ ID NOs:1-4, 10, and 11 or a fragment thereof. In yet other embodiments, the peroxidase includes an amino acid sequence having at least 80% sequence identity to one of SEQ ID NOs:20-25 or a fragment thereof.

In some embodiments, the host is a member of the genus *Bacillus* (e.g., *B. subtilis*).

In some embodiments, the one or more exogenous nucleic acid sequences is provided as an expression vector.

In some embodiments, the introducing step includes a media including a citric acid buffer or a sodium acetate buffer.

In some embodiments, the source includes lignin, lignocellulose, a guaiacyl monomer, a syringyl monomer, or a 4-hydroxyphenyl monomer. In other embodiments, the source includes one or more β-O-4 linkages.

In a second aspect, the present invention features an engineered *Bacillus* host including one or more exogenous nucleic acid sequences, where at least one exogenous nucleic acid sequence encodes (i) a fungal laccase and/or (iv) a fungal peroxidase.

In some embodiments, the at least one exogenous nucleic acid sequence encodes the laccase (e.g., a high-redox potential laccase, such as any described herein) and/or the peroxidase (e.g., a versatile peroxidase, such as any described herein). In particular embodiments, the at least one exogenous nucleic acid sequence encodes the laccase and/or the peroxidase in a sequence that is codon-optimized for the host. In some embodiments, the laccase includes an amino acid sequence having at least 80% sequence identity to one of SEQ ID NOs:1-4, 10, and 11 or a fragment thereof; and/or the peroxidase includes an amino acid sequence having at least 80% sequence identity to one of SEQ ID NOs:20-25 or a fragment thereof.

In any of the embodiments herein, the host is a member of the genus *Bacillus*. In particular embodiments, the host is a *Bacillus subtilis* bacterium.

In any of the embodiments herein, the one or more exogenous nucleic acid sequences is provided as an expression vector.

In any of the embodiments herein, the one or more exogenous nucleic acid sequences includes a nucleic acid sequence that encodes a ligninase (e.g., a laccase and/or a peroxidase) in a sequence that is codon-optimized for the host.

In any of the embodiments herein, a contiguous fragment can include at least 5, 10, 11, 12, 13, 14, 15, 16, 17, 18, 19, 20, 21, 22, 23, 24, or 25 contiguous nucleotides from a full-length nucleic acid sequence. In some embodiments, the contiguous fragment includes of from about 5 to about 100 nucleotides (e.g., from 5 to 10, 5 to 25, 5 to 50, 5 to 75, 5 to 100, 10 to 25, 10 to 50, 10 to 75, 10 to 100, 20 to 25, 20 to 50, 20 to 75, 20 to 100, 25 to 50, 25 to 75, 25 to 100, 50 to 75, 50 to 100, or 75 to 100 nucleotides).

In any of the embodiments herein, a contiguous fragment can include at least 5, 6, 7, 8, 9, 10, 11, 12, 13, 14, 15, 16, 17, 18, 19, 20, 25, 50, 75, 90, 100, 150, 200, 250, 300, or 350 contiguous amino acids from a full-length amino acid sequence. In some embodiments, the contiguous fragment includes of from about 5 to about 350 amino acids (e.g., from 5 to 10, 5 to 25, 5 to 50, 5 to 75, 5 to 100, 5 to 150, 5 to 200, 5 to 250, 5 to 300, 10 to 25, 10 to 50, 10 to 75, 10 to 100, 10 to 150, 10 to 200, 10 to 250, 10 to 300, 10 to 350, 20 to 25, 20 to 50, 20 to 75, 20 to 100, 20 to 150, 20 to 200, 20 to 250, 20 to 300, 20 to 350, 25 to 50, 25 to 75, 25 to 100, 25 to 150, 25 to 200, 25 to 250, 25 to 300, 25 to 350, 50 to 75, 50 to 100, 50 to 150, 50 to 200, 50 to 250, 50 to 300, 50 to 350, 75 to 100, 75 to 150, 75 to 200, 75 to 250, 75 to 300, and 75 to 350 amino acids).

In any embodiment herein, at least 80% sequence identity to a reference sequence can include at least 85%, 90%, 95%, 96%, 97%, 98%, or 99% sequence identity to the reference sequence (e.g., the reference nucleic acid sequence or the reference amino acid sequence).

Definitions

As used herein, the term "about" means +/−10% of any recited value. As used herein, this term modifies any recited value, range of values, or endpoints of one or more ranges.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O)Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —SO$_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —SO$_2$Ak, in which Ak is an alkyl group, as defined herein); (9) aryl; (10) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N$_3$ group); (16) cyano (e.g., a —CN group); (17) $C_{1-6}$ azidoalkyl (e.g., a —N$_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -A$^L$C(O)H, in which A$^L$ is an alkylene group, as defined herein); (20) $C_{3-8}$ cycloalkyl; (21) $C_{1-6}$ alk-$C_{3-8}$ cycloalkyl (e.g., -A$^L$Cy, in which A$^L$ is an alkylene group and Cy is a cycloalkyl group, as defined herein); (22) halo (e.g., F, Cl, Br, or I); (23) C$_{1-6}$ haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) C$_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) C$_{1-6}$ nitroalkyl (e.g., an alkyl group, as defined herein, substituted by one to three nitro groups); (31) N-protected amino; (32) N-protected amino-C$_{1-6}$ alkyl; (33) oxo (e.g., an =O group); (34) C$_{1-6}$ thioalkoxy (e.g., —SAk, in which Ak is an alkyl group, as defined herein); (35) thio-C$_{1-6}$ alkoxy-C$_{1-6}$ alkyl (e.g., an alkyl group, which is substituted by an thioalkoxy group —SAk, in which Ak is an alkyl group, as defined herein); (36) —(CH$_2$)$_r$CO$_2$R$^A$, where r is an integer of from zero to four, and R$^A$ is selected from the group consisting of (a) hydrogen, (b) C$_{1-6}$ alkyl, (c) C$_{4-18}$ aryl, and (d) C$_{1-6}$ alk-C$_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) C$_{1-6}$ alkyl, (c) C$_{4-18}$ aryl, and (d) C$_{1-6}$ alk-C$_{4-18}$ aryl; (38) —(CH$_2$)$_r$SO$_2$R$^D$, where r is an integer of from zero to four and where R$^D$ is selected from the group consisting of (a) C$_{1-6}$ alkyl, (b) C$_{4-18}$ aryl, and (c) C$_{1-6}$ alk-C$_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) C$_{1-6}$ alkyl, (c) C$_{4-18}$ aryl, and (d) C$_{1-6}$ alk-C$_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) C$_{1-6}$ alkyl, (d) C$_{2-6}$ alkenyl, (e) C$_{2-6}$ alkynyl, (f) C$_{4-18}$ aryl, (g) C$_{1-6}$ alk-C$_{4-18}$ aryl, (h) C$_{3-8}$ cycloalkyl, and (i) C$_{1-6}$ alk-C$_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., OA$^L$Cy, in which A$^L$ is an alkylene group and Cy is a cycloalkyl group, as defined herein); and (47) arylalkoxy (e.g., —OA$^L$Ar, in which A$^L$ is an alkylene group and Ar is an aryl group, as defined herein). In particular embodiments, an unsubstituted aryl group is a C$_{4-18}$, C$_{4-14}$, C$_{4-12}$, C$_{4-10}$, C$_{6-18}$, C$_{6-14}$, C$_{6-12}$, or C$_{6-10}$ aryl group.

By "aryloxy" is meant —OR, where R is an optionally substituted aryl group, as described herein. Exemplary aryloxy groups include phenoxy or naphthyloxy. The aryloxy group can be substituted or unsubstituted. For example, the aryloxy group can be substituted with one or more substitution groups, as described herein for aryl. Exemplary unsubstituted aryloxy groups include C$_{4-18}$, C$_{4-14}$, C$_{4-12}$, C$_{4-10}$, C$_{6-18}$, C$_{6-14}$, C$_{6-12}$, or C$_{6-10}$ aryloxy groups.

By "hydroxyl" is meant —OH.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkylsulfonate with reactive group O), such as —SO$_2$—R$^{S1}$, where R$^{S1}$ is optionally substituted C$_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted C$_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted C$_1$-12 alkyl or optionally substituted C$_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{T2}$)$_3$, where each R$^{T2}$ is, independently, optionally substituted C$_{1-12}$ alkyl or optionally substituted C$_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenylsulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methyl sulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. For any nucleic acid sequence described herein, uracil (U) may be thymine (T), and T may be U.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, $N^4$-acetylcytidine, 5-formylcytidine, $N^4$-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, $N^6$-methyladenosine, $N^6$-isopentenyladenosine, $N^6$-(cis-hydroxy-isopentenyl)adenosine, 2-methylthio-$N^6$-(cis-hydroxyisopentenyl) adenosine, $N^6$-glycinylcarbamoyladenosine, $N^6$-threonylcarbamoyladenosine, 2-methylthio-$N^6$-threonyl carbamoyladenosine, $N^6,N^6$-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, $N^2$-methylguanosine, $N^2,N^2$-dimethylguanosine, 8-oxo-guanosine, 7-methyl-8-oxo-guanosine, 1-methyl-6-thio-guanosine, $N^2$-methyl-6-thio-guanosine, and $N^2,N^2$-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, 2'-bromo, or 2-iodo), 2'-alkyl (e.g., 2'-methyl, 2'-ethyl, 2'-propyl, 2'-allyl, etc., in which alkyl can be an optionally substituted alkyl, as defined herein), 2'-aryl (e.g., 2'-phenyl, in which aryl can be an optionally substituted aryl, as defined herein), 2'-alkaryl (e.g., 2'-benzyl, in which alkaryl can be an aryl group, as defined herein, attached to the parent molecular group through an alkylene group, in which an alkylene group can be a multivalent (e.g., bivalent, trivalent, tetravalent, etc.) form of an alkyl group, as described herein), 2'-amino (e.g., 2'-NH$_2$, etc., in which amino can be NR$^{N1}$R$^{N2}$ where each of R$^{N1}$ and R$^{N2}$ is, independently, H, alkyl, or alkaryl, or R$^{N1}$ and R$^{N2}$, taken together with the nitrogen atom to which each are attached, form a heterocyclyl group), 2'-alkoxy (e.g. 2'-O-methoxy, 2'-O-ethoxy, etc., in which alkoxy can be —OR, where R is an optionally substituted alkyl group, as described herein), 2'-alkylamino (e.g., 2'-O-methylamino, 2'-O-ethylamino, etc.), 2'-O-alkylamino (e.g., 2'-O-methylamino, 2'-O-ethylamino, etc., in which alkylamino can be an alkyl group, as defined herein, substituted by an amino group, as defined herein), 2'-azido (in which azido is an —$N_3$ group), 2'-O-cyanoalkyl (e.g., 2'-O-cyanomethyl, etc., in which cyanoalkyl can be an alkyl group, as defined herein, substituted by a cyano group (a —CN group)), 2'-O-alkoxyalkyl (e.g., 2'-O-(2-methoxyethyl), etc., in which alkoxyalkyl can be an alkyl group, as defined herein, which is substituted with an alkoxy group, as defined herein), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques in Biochemistry and Molecular Biology-Hybridization with Nucleic Acid Probes Part 1, Second Chapter, "Overview of principles of hybridization and the strategy of nucleic acid probe assay," Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. A "complement" can include a "reverse complement," in which a given sequence is reversed to provide a reverse sequence and then a complement, as defined herein, of that reverse sequence provides a reverse complement. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (G), alanine (A), valine (V), leucine (L), and isoleucine (I); a group of amino acids having aliphatic-hydroxyl side chains consists of serine (S) and threonine (T); a group of amino acids having amide containing side chains consisting of asparagine (N) and glutamine (Q); a group of amino acids having aromatic side chains consists of phenylalanine (F), tyrosine (Y), and tryptophan (W); a group of amino acids having basic side chains consists of lysine (K), arginine (R), and histidine (H); a group of amino acids having acidic side chains consists of glutamic acid (E) and aspartic acid (D); and a group of amino acids having sulfur containing side chains consists of cysteine (C) and methionine (M). Exemplary conservative amino acid substitution groups are valine-leucine-isoleucine (VLI), phenylalanine-tyrosine (FY), lysine-arginine (KR), alanine-valine (AV), glycine-serine (GS), glutamate-aspartate (ED), and asparagine-glutamine (NQ), as well as any described herein. Accordingly, for any polypeptide sequence described herein, the present invention may also encompass one or more conservative amino acid substitutions.

For any polypeptide sequence described herein, the present invention may also encompass a conservative subset, which can include a conservation between groups of strongly similar properties or a conservation between groups of weakly similar properties, as described herein. Exemplary conservative subsets include those having a conservation between groups of strongly similar properties, e.g., a group containing serine-threonine-alanine (STA), asparagine-glutamate-glutamine-lysine (NEQK), asparagine-histidine-glutamine-lysine (NHQK), asparagine-aspartate-glutamate-glutamine (NDEQ), glutamine-histidine-arginine-lysine (QHRK), methionine-isoleucine-leucine-valine (MILV), methionine-isoleucine-leucine-phenylalanine (MILF), histidine-tyrosine (HY), or phenylalanine-tyrosine-tryptophan (FYW); as well as those having a conservation between groups of weakly similar properties, e.g., a group containing cysteine-serine-alanine (CSA), alanine-threonine-valine (ATV), serine-alanine-glycine (SAG), serine-threonine-asparagine-lysine (STNK), serine-threonine-proline-alanine (STPA), serine-glycine-asparagine-aspartate (SGND), serine-asparagine-aspartate-glutamate-glutamine-lysine (SNDEQK), asparagine-aspartate-glutamate-glutamine-histidine-lysine (NDEQHK), asparagine-glutamate-glutamine-histidine-arginine-lysine (NEQHRK), phenylalanine-valine-leucine-isoleucine-methionine (FVLIM), or histidine-phenylalanine-tyrosine (HFY).

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, CLUSTAL OMEGA, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length amino acid sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "host," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

As used herein, the term "exogenous" in reference to a nucleic acid or a polypeptide refers to a nucleic acid or a polypeptide that is not normally or naturally found in and/or produced by a given bacterium, organism, or cell in nature. As used herein, the term "endogenous" in reference to a nucleic acid or a polypeptide refers to a nucleic acid or a polypeptide that is normally found in and/or produced by a given bacterium, organism, or cell in nature.

By "linker" is meant any useful multivalent (e.g., bivalent) component useful for joining to different portions or segments. Exemplary linkers include a nucleic acid sequence, a chemical linker (e.g., an alkylene group such as a multivalent (e.g., bivalent, trivalent, tetravalent, etc.) form of an alkyl group, as described herein; a heteroalkylene group such as a divalent form of an alkylene group, as defined herein, containing one, two, three, or four non carbon heteroatoms (e.g., independently selected from the group consisting of nitrogen, oxygen, phosphorous, sulfur, or halo); or an ethylene glycol group, e.g., —$OCH_2CH_2$—, including a poly(ethylene glycol) (PEG) group —$(OCH_2CH_2)_n$—, in which n is any useful number in any of these (e.g., any useful n to provide any useful number average molar mass $M_n$)), etc.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence. Exemplary promoter sequences can include a nucleic acid regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters can contain Shine-Dalgarno sequences in addition to the −10 and −35 consensus sequences.

An "expression control sequence" can be a nucleic acid sequence that controls and regulates the transcription and translation of another nucleic acid sequence. A coding sequence is "under the control" of transcriptional and translational control sequences in a cell when RNA polymerase transcribes the coding sequence into mRNA, which is then translated into the protein encoded by the coding sequence. Exemplary transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIGS. 1A-1F exemplary protein sequences for exemplary laccase enzymes (SEQ ID NOs:1-4, 10, and 11).

FIGS. 2A-2F exemplary protein sequences for exemplary peroxidase enzymes (SEQ ID NOs:20-25).

DETAILED DESCRIPTION OF THE INVENTION

Figure 3:
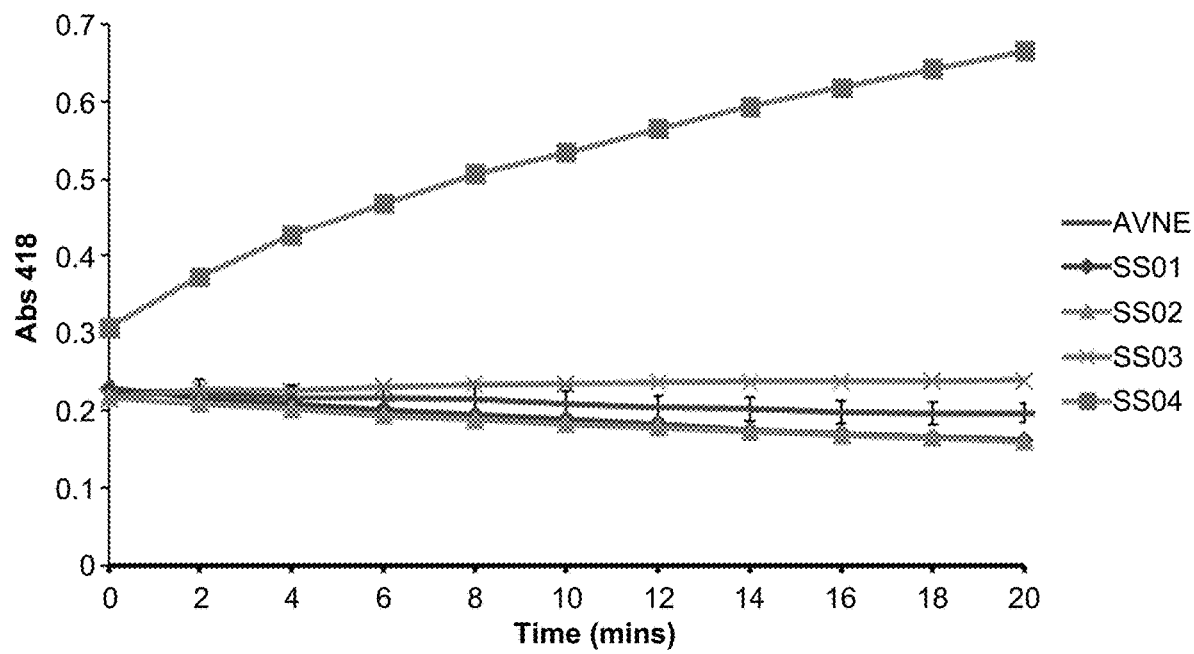
FIG. 3 provides screening for ligninase (laccase or versatile peroxidase) activity in the engineered strains with 2,2'-azino-bis(3-ethylbenzothiazoline-6-sulphonic acid) (ABTS) as the substrate. To screen for versatile peroxidase activity, $H_2O_2$ was included in the corresponding reactions. The graph shows the absorbance of the ABTS assay product at different time points in AVNE, SS01, SSO2, SS03 and SS04. Higher antioxidant activity was observed in SS04 strain having codon optimized peroxidase, as compared to other strains.

The present invention relates, in part, to methods and compositions (e.g., engineered hosts) for use in degrading ether linkages in lignin. In particular embodiments, the methods include use of a buffer, such as for example and without limitation, a citric acid buffer (e.g., a citric acid—$Na_2HPO_4$ buffer, a citric acid-sodium citrate buffer) or an acetic acid buffer (e.g., a sodium acetate-acetic acid buffer).

Methods and engineered hosts can include one or more exogenous ligninases. In particular embodiments, the ligninase is a phenol oxidase (e.g., a laccase). Such phenol oxidases can be employed to react with a functional group present in lignin (or a derivative thereof) in an oxidation reaction. In particular embodiments, the phenol oxidase results in the formation of a phenoxy radical, which in turn can result in aryl-alkyl cleavage, $C_\alpha$-$C_\beta$ cleavage, carbonyl formation (e.g., at $C_\alpha$), quinone formation, and/or polymerization (e.g., between the radical and another reactive group).

Further exemplary laccase can include a sequence having at least 80% sequence identity to SEQ ID NO:1. In particular embodiments, the laccase has one or more mutations, e.g., V162A, H208Y, S224G, A239P, D281E, S426N, and/or A461T, as compared to corresponding location(s) in SEQ ID NO:1 or a sequence optimally aligned to SEQ ID NO:1. In other embodiments, the laccase has one or more mutations, e.g., D205N, F396I, S426D, I452V, F454E, F454P, F454T, F454A, F454G, F454R, and/or T487S, as compared to corresponding location(s) in SEQ ID NO:1 or a sequence optimally aligned to SEQ ID NO:1. In yet other embodiments, the laccase has one or more mutations, e.g., N181D, A361T, V286L, P393H, P486L, F454S, S482L, and/or P486L as compared to corresponding location(s) in SEQ ID NO:1 or a sequence optimally aligned to SEQ ID NO:1. Any one or more these mutations can be combined within a sequence.

Further exemplary laccase can include a sequence having at least 80% sequence identity to SEQ ID NO:10. In particular embodiments, the laccase has one or more mutations, e.g., N208S, R280H, N331D, D341N, and/or P394H, as compared to corresponding location(s) in SEQ ID NO:1 or a sequence optimally aligned to SEQ ID NO:10. In other embodiments, the laccase has one or more mutations, e.g., L46I, F81S, N130D, S135G, D255G, A240P, T294I, K324M, F332S, T428A, N443S, I453V, and/or D490G, as compared to corresponding location(s) in SEQ ID NO:1 or a sequence optimally aligned to SEQ ID NO:10. Any one or more of these mutations can be combined within a sequence.

Yet other laccases include Lac from Basidiomycete PM1 (e.g., such as an amino acid sequence provided as UniProt Accession No. Q12571 or a fragment thereof), Lac from *Trametes hirsuta* (e.g., such as an amino acid sequence provided as UniProt Accession No. B2L9C1 or a fragment thereof), Lac1 from *Trametes* sp. C30 (e.g., such as an amino acid sequence provided as UniProt Accession No. Q9UVQ5 or a fragment thereof), Lac1 from *Coriolopsis gallica* (e.g., such as an amino acid sequence provided as UniProt Accession No. Q1W6B1 or a fragment thereof), Lac1 from *Pycnoporus cinnabarinus* (e.g., such as an amino acid sequence provided as UniProt Accession No. Q9UVQ2 or a fragment thereof), LacA from *Trametes* sp. AH28-2 (e.g., such as an amino acid sequence provided as UniProt Accession No. Q5MBH6 or a fragment thereof), LacIII from *Trametes versicolor* (e.g., such as an amino acid sequence provided as UniProt Accession No. Q8TFM1 or a fragment thereof), Lap2 from *Trametes pubescens* (e.g., such as an amino acid sequence provided as UniProt Accession No. Q8TG94 or a fragment thereof), Lcc1 from *Trametes sanguinea* (e.g., such as an amino acid sequence provided as UniProt Accession No. C9WKP8 or a fragment thereof), Lcc1 from *Lentinus tigrinus* (e.g., such as an amino acid sequence provided as UniProt Accession No. Q5EBY5 or a fragment thereof), Lcc1 from *Pycnoporus coccineus* (e.g., such as an amino acid sequence provided as UniProt Accession No. Q96TR6 or a fragment thereof), Lcc1 from *Coriolopsis trogii* (e.g., such as an amino acid sequence provided as UniProt Accession No. Q9HDQ0 or a fragment thereof), Lcc1 from *Coriolopsis rigida* (e.g., such as an amino acid sequence provided as UniProt Accession No. C7FH95 or a fragment thereof), and Pox2 from *Trametes* sp. 1-62 (e.g., such as an amino acid sequence provided as UniProt Accession No. Q716A1 or a fragment thereof).

In other embodiments, the ligninase is a peroxidase (e.g., a versatile peroxidase (VP), lignin peroxidase (LiP), or manganese peroxidase (MnP)). Such peroxidases can be employed to generate a radical group in an oxidation reaction (e.g., in the presence of hydrogen peroxide), which can further result in C—C oxidative cleavage (e.g., cleavage of a (3-1 linkage).

Further exemplary VP can include a sequence having at least 80% sequence identity to SEQ ID NO:20. In particular embodiments, the VP has one or more mutations, e.g., E37K, V160A, T184M, and/or Q202L, as compared to corresponding location(s) in SEQ ID NO:20 or a sequence optimally aligned to SEQ ID NO:20. In particular embodiments, the VP has one or more mutations, e.g., H39R, D213A, and/or G330R, as compared to corresponding location(s) in SEQ ID NO:20 or a sequence optimally aligned to SEQ ID NO:20. In yet other embodiments, the VP has one or more other mutations, e.g., N11D, D22N, G35K, H39R, E40K, T45A, D82G, E83K, E83G, E83S, E83V, S86R, K89E, K89M, I103V, G107S, E140G, P141A, P182S, P182H, G183E, T184D, T184S, F186L, D213A, N214Y, Q219R, Q229P, T323I, and/or G330R, as compared to corresponding location(s) in SEQ ID NO:20 or a sequence optimally aligned to SEQ ID NO:20. Any one or more of these mutations can be combined within a sequence.

Yet other peroxidases include a peroxidase (e.g., GP11 from *Auricularia subglabra* (strain TFB-10046/SS5), such as an amino acid sequence provided as UniProt Accession No. J0WUI3 or a fragment thereof; Lgp3 from *Phlebia radiata*, such as an amino acid sequence provided as UniProt Accession No. Q53WT9 or a fragment thereof; LiPBad from *Bjerkandera adusta*, such as an amino acid sequence provided as UniProt Accession No. W8YN06 or a fragment thereof; MnP4 from *Pleurotus ostreatus*, such as an amino acid sequence provided as UniProt Accession No. A0A067NYV2 or a fragment thereof; MnP5 from *Pleurotus pulmonarius*, such as an amino acid sequence provided as UniProt Accession No. Q2VT17 or a fragment thereof; VP3 from *Pleurotus ostreatus*, such as an amino acid sequence provided as UniProt Accession No. A0A067NKY1 or a fragment thereof); VpBad from *Bjerkandera adusta*, such as an amino acid sequence provided as UniProt Accession No. W8YE46 or a fragment thereof; VPL1 from *Pleurotus eryngii*, such as an amino acid sequence provided as UniProt Accession No. Q9UR19 or a fragment thereof; VPL2 from *Pleurotus eryngii*, such as an amino acid sequence provided as UniProt Accession No. 094753 or a fragment thereof; VPL3 from *Pleurotus eryngii*, such as an amino acid sequence provided as UniProt Accession No. Q8J1S4 or a fragment thereof; and VPS1 from *Pleurotus eryngii*, such as an amino acid sequence provided as UniProt Accession No. Q9UVP6 or a fragment thereof); a manganese peroxide (e.g., MnP1 from *Phanerochaete chrysosporium*, such as an amino acid sequence provided as UniProt Accession No. Q02567 or a fragment thereof; and MnP2 from *Phlebia radiata*, such as an amino acid sequence provided as UniProt Accession No. Q70LM3 or a fragment thereof); and ligninase (e.g., LiPH8 from *Phanerochaete chrysosporium*, such as an amino acid sequence provided as UniProt Accession No. P06181 or a fragment thereof).

Any of the ligninases and enzymes herein include fusion or chimeric proteins. Such fusion proteins can include an amino acid sequence from a particular ligninase (e.g., any sequence or ligninase herein) and one or more leader sequences (e.g., leader peptides, signaling peptides, proleader peptides, pre-proleader peptides, etc., from any useful organism). In one non-limiting embodiment, a fusion protein includes a leader sequence that is endogenous to the host and a ligninase sequence that is exogenous to the host (e.g., a fungal ligninase sequence). Exemplary chimeric proteins can include an amino acid sequence from a first ligninase or a fragment thereof (e.g., any sequence or ligninase herein) and an amino acid sequence from a second ligninase or a fragment thereof (e.g., any sequence or ligninase herein), thereby forming a hybrid sequence.

Yet other ligninases and accessory enzymes can include an aromatic peroxygenase, an aryl alcohol dehydrogenase, an aryl alcohol oxidase, an aryl alcohol peroxidase, a catechol 2,3-dioxygenase, a cellobiose dehydrogenase, a Cα-dehydrogenase, an O-demethylase, a dye-decolorizing peroxidase, a β-etherase, a glyoxal oxidase, a glucose dehydrogenase, a glutathione lyase, a heme-thiolate haloperoxidase, a high-redox potential laccase, a hydrogen peroxide-generating oxidase, a perhydrolase, a pyranose 2-oxidase, a quinone reductase, an unspecific peroxygenase, a xylanase, etc.

Ligninases can be derived from any useful source, such as fungus, e.g., ascomycetes (e.g., *Botrytis aclada*, *Botrytis cinerea*, *Chaetomium thermophile*, *Coniophora puteana*, *Magnaporthe grisea*, *Melanocarpus albomyces*, *Myceliophthora thermophila*, *Myrothecium verrucaria*, *Neurospora crassa*, *Trichoderma atroviride*, *Trichoderma harzianum*, *Trichoderma longibrachiatum*, *Trichoderma reesei*, *Trichoderma viride*, etc.), basidiomycetes (e.g., *Bjerkandera adusta*, *Bjerkandera fumosa*, *Bjerkandera* sp. (e.g., strain BOS55, B33/3, etc.), *Cerrena unicolor*, *Coprinus cinereus*, *Cyathus bulleri*, *Fomitopsis palustris*, *Lentinus tigrinus*, *Lenzitis betulina*, *Panus tigrinus*, *Phanerochaete chrysosporium*, *Phlebia radiata*, *Pleurotus eryngii*, *Pleurotus ostreatus*, *Pleurotus pulmonarius*, *Pycnoporus cinnabarinus*, *Pycnoporus coccineus*, *Pycnoporus sanguineus*, *Rigidoporus lignosus*, *Scytalidium thermophilum*, *Stereum ostrea*, *Theliophora terristrus*, *Trametes pubescens*, *Trametes suaveolens*, *Trametes versicolor*, *Trametes villosa*, etc.), deuteromycetes (e.g., *Rhizoctonia solani*), and anaerobic species (e.g. *Orpinomyces* sp.). In particular embodiments, one or more ligninases are derived from a white-rot fungus (e.g., *Ceriporiopsis subvermispora*, *Coriolus versicolor*, *Cyathus stercoreus*, *Heterobasidion annosum*, *Irpex lacteu*, *Phanerochaete chrysosporium* (*Sporotrichum pulverulentum*), *Phellinus pini*, *Phlebia radiata*, *Phlebia* spp., *Pleurotus ostreatus*, *Pleurotus* spp., *Trametes versicolor*, etc.).

Such ligninases can further include the use of one or more mediators, cofactors, or metals (e.g., metal ions), such as heme, cadmium ($Cd^{2+}$), calcium (e.g., $Ca^{2+}$), copper (e.g., $Cu^{2+}$), iron, manganese (e.g., $Mn^{2+}$), potassium (e.g., $K^+$), an alcohol (e.g., including a diol, a polyol, a phenol, veratryl alcohol, catechol, guaiacol, etc.), an aromatic group (e.g., an aniline, xylidine, anisidine, etc.), an ammonium (e.g., ammonium tartrate), an azole (e.g., imidazole or hydroxybenzotriazole), a chelator (e.g., an organic acid), a fatty acid (e.g., an unsaturated fatty acid), a fungicide (e.g., cyclohex-imide), a hydroxyamine (e.g., a chemical compound having a N—OH functional group), a lignin-derived mediator (e.g., acetosyringone, acetovanillone, p-coumaric acid, ferulic acid, sinapic acid, syringaldehyde, and vanillin), a peroxide (e.g., $H_2O_2$), a redox molecule (e.g., 2,2'-azino-bis-(3-eth-ylbenzothiazoline-6-sulphonic acid) (ABTS), N-hydroxyac-etanilide (NHA), 3-hydroxyanthranilic acid (HAA), N-hy-droxybenzotriazole (HBT), N-hydroxyphtalimide (HPI), syringic acid, 2,2,6,6-tetramethylpiperidine-1-yloxy (TEMPO), and violuric acid (VLA)), a thiol, etc.

Exemplary enzyme(s) (e.g., nucleic acid sequences encoding such enzyme(s)) can be provided as one or more exogenous nucleic acid sequences. In one instance, an enzyme is provided (e.g., encoded) in separate exogenous nucleic acid sequences. For example and without limitation, first enzyme is provided in a first exogenous nucleic acid sequence, and a second enzyme is provided in a second exogenous nucleic acid sequence. In another instance, two or more enzymes are provided in a single exogenous nucleic acid sequence. For example and without limitation, a first enzyme and a second enzyme are provided (e.g., encoded) in a first exogenous nucleic acid sequence. A first sequence encoding the first enzyme can be operably linked to a second sequence encoding the second enzyme. In one non-limiting instance, the exogenous nucleic acid sequence encodes two or more enzymes in a contiguous sequence.

The exogenous nucleic acid can be provided in any useful form (e.g., a vector, a phage, a plasmid, etc.). In particular embodiments, the exogenous nucleic acid is provided as an inserted sequence within a vector (e.g., any useful vector, such that those described herein, such as pHT254, pHT253, and pHT255).

The exogenous nucleic acid can include any other useful portions, such as binding sites (e.g., ribosome binding sites), promoter regions, portions for encoding one or more peptides (e.g., signal peptides, secretory signal peptides, fusion proteins, peptide tags, affinity tags, solubility tags, etc.), etc. Exemplary signal peptides include, e.g., secretory signal peptides, as well as any described herein. Further non-limiting signal peptides (SPs) can include one or more of subtilisin E secretory SP (AprE SP, such as amino acid sequences provided as UniProt Accession Nos. P04189, G4EY69, L8AEF2, and A0A164SYK1 or a fragment thereof (e.g., amino acids 1-29)), alpha-amylase SP (AmyE SP, such as amino acid sequences provided as UniProt Accession Nos. P00691, G4F096, and C0KWE6 or a fragment thereof (e.g., amino acids 1-27 or 1-33)), extracellular zinc metal-loprotease SP (NprE SP, such as amino acid sequences provided as UniProt Accession Nos. P68736, P68735, and P68734 or a fragment thereof (e.g., amino acids 1-27)), YfhK SP (e.g., such as amino acid sequences provided as UniProt Accession Nos. O31579 and L8AE42 or a fragment thereof (e.g., amino acids 1-27 or 1-29)), YlxW SP (e.g., such as amino acid sequences provided as UniProt Accession Nos. C0SPA3, A0A164SIA0, and A0A1B2B3N6 or a fragment thereof (e.g., amino acids 1-34)), endopeptidase SP (e.g., YojL SP, such as amino acid sequences provided as UniProt Accession Nos. O31852 and A0A164XYX0 or a fragment thereof (e.g., amino acids 1-26)), YpjP SP (e.g., such as amino acid sequences provided as UniProt Accession Nos. P54172 and A0A086DP91 or a fragment thereof (e.g., amino acids 1-26 or 1-29)), YwmC SP (e.g., such as amino acid sequences provided as UniProt Accession Nos. P70960 and A0A0A1MKV7 or a fragment thereof (e.g., amino acids 1-23)), YwmD SP (e.g., such as amino acid sequences provided as UniProt Accession Nos. P70961 and A0A164VBM2 or a fragment thereof (e.g., amino acids 1-23 or 1-34)), cell wall-binding protein SP (e.g., YwsB SP, such as amino acid sequences provided as UniProt Accession Nos. P96729 and A0A164VDT0 or a fragment thereof (e.g., amino acids 1-30)), YxaK SP (e.g., such as amino acid sequences provided as UniProt Accession Nos. P42111, A0A162R595, and A0A1D8FNT7 or a fragment thereof (e.g., amino acids 1-41 or 1-42)), or a fragment thereof (e.g., a fragment including amino acids 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, or 1-42 of the amino acid sequences provided herein as any of the UniProt Accession Nos. listed herein). Additional details regarding sequences of SPs and methods of incorporating such SPs are provided in Brockmeier U et al., "Systematic screening of all signal peptides from *Bacillus subtilis*: a powerful strategy in optimizing heterologous protein secretion in Gram-positive bacteria," *J. Molec. Biol.* 2006; 362(3):393-402, which is incorporated herein by reference in its entirety.

Further non-limiting ligninases are described in Alcade M, "Engineering the ligninolytic enzyme consortium," *Trends Biotechnol.* 2015; 33:155-162; Alcade M, "Laccases: Biological Functions, Molecular Structure and Industrial Applications," Chapter 26 in *Industrial Enzymes* (J. Polaina and A P MacCabe, eds.), Springer (Dordrecht, the Netherlands), 2007, pp. 461-76; Camarero S et al., "Engineering platforms for directed evolution of laccase from *Pycnoporus cinnabarinus,*" *Appl. Environ. Microbiol.* 2012; 78:1370-84; Dashtban M et al., "Fungal biodegradation and enzymatic modification of lignin," *Int. J. Biochem. Mol. Biol.* 2010; 1:36-50; Desai S S et al., "Microbial laccases and their applications: a review," *Asian J. Biotechnol.* 2011; 3:98-124; Falade A O et al., "Lignin peroxidase functionalities and prospective applications," *Microbiol. Open* 2017; 6:e00397 (14 pp.); Fisher A B et al., "Lignin biodegradation and industrial applications," AIM Bioeng. 2014; 1:92-112; Gar-cia-Ruiz E et al., "Directed evolution of a temperature-, peroxide- and alkaline pH-tolerant versatile peroxidase," Biochem. J. 2012; 441:487-98; Gonzalez-Perez D et al., "Structural determinants of oxidative stabilization in an evolved versatile peroxidase," *ACS Catal.* 2014; 4:3891-901; Gonzalez-Perez D et al., "The making of versatile peroxidase by directed evolution," *Biocatal. Biotransform.* 2017; 36:1-11; Gonzalez-Perez D et al., "Assembly of evolved ligninolytic genes in *Saccharomyces cerevisiae,*" *Bioengineered* 2014; 5:254-63; Gonzalez-Perez D et al., "Alkaline versatile peroxidase by directed evolution," *Catal. Sci. Technol.* 2016; 6:6625-36; Gonzalez-Perez D et al., "*Saccharomyces cerevisiae* in directed evolution: an efficient tool to improve enzymes," *Bioengineered* 2012; 3:172-7; Janusz G et al., "Lignin degradation: microorganisms, enzymes involved, genomes analysis and evolution," *FEMS Microbiol. Rev.* 2017; 41:941-62; Kunamneni A et al., "Laccases and their applications: a patent review," *Recent Patents Biotechnol.* 2008; 2:10-24; Kunamneni A et al., "Engineering and applications of fungal laccases for organic synthesis," *Microbial Cell Factories* 2008; 7:32 (17 pp.); Li K et al., "Comparison of fungal laccases and redox mediators in oxidation of a nonphenolic lignin model compound," *Appl. Environ. Microbiol.* 1999; 65:2654-60; Martinez A, "High Redox Potential Peroxidases," Chapter 27 in *Industrial Enzymes* (J. Polaina and AP MacCabe, eds.), Springer (Dordrecht, the Netherlands), 2007, pp. 477-88; Maté D et al., "Laboratory evolution of high-redox potential laccases," *Chem. Biol.* 2010; 17:1030-41; Mate D M et al., "Blood tolerant laccase by directed evolution," *Chem. Biol.* 2013; 20:223-31; Mate D M et al., "Laccase engineering: from rational design to directed evolution," *Biotechnol. Adv.* 2015; 33:25-40; Mate D M et al., "Laccase: a multi-purpose biocatalyst at the forefront of biotechnology," *Microbial Biotechnol.* 2017; 10:1457-67; Munk L et al., "Can laccases catalyze bond cleavage in lignin?," *Biotechnol. Adv.* 2015; 33:13-24; Pardo I et al., "Development of chimeric laccases by directed evolution," *Biotechnol. Bioeng.* 2012; 109:2978-86; Pollegioni L et al., "Lignin-degrading enzymes," *FEBS J.* 2015; 282:1190-213; Tian X F et al., "Impact and prospective of fungal pre-treatment of lignocellulosic biomass for enzymatic hydrolysis," *Biofuels Bioprod. Bioref.* 2012; 6:335-50; and Wang Y et al., "Plant cell wall lignification and monolignol metabolism," *Front. Plant Sci.* 2013; 4:220 (14 pp.), each of which is incorporated herein by reference in its entirety.

Microbial Hosts

The present invention relates, in part, to engineered microbial hosts. Such hosts can be derived from any useful microorganism, which can include prokaryotic and eukaryotic microbial species from the domains Archaea, Bacteria, and Eukaryote, the latter including yeast and filamentous fungi, protozoa, algae, or higher Protista. The terms "cell," "microbial cells," and "microbes" are used interchangeably with the term microorganism. The term "host" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In some non-limiting instance, the microbial host is a Gram-positive bacterium. Exemplary Gram-positive bacteria include cocci, nonsporulating rods, and sporulating rods. The genera of Gram-positive bacteria include, for example, *Actinomyces, Bacillus, Clavibacter, Clostridium, Corynebacterium, Enterococcus, Erysipelothrix, Lactobacillus, Leifsonia, Listeria, Mycobacterium, Nocardia, Rathybacter, Staphylococcus, Streptococcus,* and *Streptomyces.*

Such hosts can be transformed to provide an engineered host. Exemplary methods of transformation can include delivery of one or more exogenous nucleic acids in any useful form (e.g., as a vector, plasmid, phage, etc.) in any useful manner (e.g., sonoporation, electroporation, particle-based carriers, vectors, etc.) to the host.

Exogenous Nucleic Acids and Proteins

Hosts can be engineered to include an exogenous nucleic acid (e.g., any described herein), in which expression of such an exogenous nucleic acid produces exogenous proteins (e.g., any described herein). The term "heterologous" or "exogenous" as used herein with reference to nucleic acids and amino acids (e.g., enzymes), indicates nucleic acids and amino acids that are expressed in an organism other than the organism from which they originated or are found in nature, independently on the level of expression that can be lower, equal to, or higher than the level of expression of the molecule in the native microorganism. An exogenous nucleic acid may be from a different species (and so heterologous) or from the same species (and so homologous), relative to the cell being transformed. Thus, an exogenous nucleic acid (e.g., a gene) can include a homologous nucleic acid that occupies a different location in the genome of the cell or is under different control, relative to the endogenous copy of the nucleic acid. An exogenous nucleic acid may be present in more than one copy in the cell. An exogenous nucleic acid may be maintained in a cell as an insertion into the genome (nuclear or plastid) or as an episomal molecule.

In some embodiments, the exogenous nucleic acid is a nucleic acid that has been generated via human intervention, including by recombinant means or direct chemical synthesis, with a series of specified nucleic acid elements that permit transcription and/or translation of a particular nucleic acid in a host cell. The exogenous nucleic acid (e.g., an expression vector or an expression cassette) may be part of a plasmid, virus, or nucleic acid fragment. One of skill in the art understands that a "recombinant nucleic acid" that encodes a particular gene, or portion thereof, is isolated from the specific context in which it naturally occurs.

In particular embodiments, the exogenous nucleic acid includes one or more coding sequences (e.g., a nucleic acid to be transcribed) that is in operable linkage with a promoter (e.g., any described herein). In other embodiments, the coding sequence is in operable linkage with a control element (e.g., one or more promoters, enhancers, transcription termination sequences, and translation initiation sequences). In some embodiments, the exogenous nucleic acid includes a coding sequence and a promoter, optionally in combination with one or more control sequences. Expression cassettes for enzymes include, for example and without limitation, a translation initiation control sequence.

Exemplary promoters include a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which may be located as much as several thousand base pairs from the start site of transcription.

An exogenous nucleic acid may be present or provided as a vector. Exemplary, non-limiting vectors include pHT254, pHT253, and pHT255, each of which is available from MoBiTec GmbH (Goettingen, Germany). Methods for employing such vectors are known, see, e.g., Phan T T et al., "Development of Pgrac100-based expression vectors allowing high protein production levels in *Bacillus subtilis* and relatively low basal expression in *Escherichia coli,*" *Microb. Cell Fact.* 2015; 14:72 (9 pp.); and Phan T T et al., "Development of a strong intracellular expression system for *Bacillus subtilis* by optimizing promoter elements," *J. Biotechnol.* 2012; 157(1):167-172, each of which is incorporated herein by reference in its entirety.

Sources

Exemplary sources include lignin or a lignin derivative (e.g., formed from a combination of one or more monomers, such as a monolignol monomer, a p-coumaryl alcohol or an alkoxyl form thereof (e.g., a methoxylated form, including mono- and di-methoxylated forms), a coniferyl alcohol or an alkoxyl form thereof (e.g., a methoxylated form), a coumaryl alcohol of an alkoxyl form thereof (e.g., a methoxylated form), and a sinapyl alcohol or an alkoxyl form thereof (e.g., a methoxylated form)). In other embodiments, lignin or a lignin derivative can be characterized by the presence of one or more aromatic functional groups, such as a p-hydroxyphenyl group, a guaiacyl group, and/or a syringyl group.

Lignin can have different compositions depending on the plant material from which the lignin is derived. Exemplary lignin can include softwood lignin (e.g., derived from softwood and including of from about 25% to about 30% (w/w) of lignin), compression wood lignin (e.g., derived from compression wood and including of from about 35% to about 40% (w/w) of lignin), typical hardwood lignin (e.g., derived from hardwood and including of from about 20% to about 25% (w/w) of lignin), tropical hardwood lignin (e.g., derived from tropical hardwood and including of from about 30% to about 40% (w/w) of lignin), tension wood lignin (e.g., derived from tension wood and including of from about 20% to about 25% (w/w) of lignin), wheat lignin (e.g., derived from wheat, including any useful part of plant, such as the root, leaves, shoots, and/or stems), maize lignin (e.g., derived from maize, including any useful part of plant, such as the root, leaves, shoots, and/or stems; and including of from about 20% to 75% (w/w) of lignin), mixed grasses lignin (e.g., derived from mixed grasses, including any useful part of plant, such as the root, leaves, shoots, and/or stems).

The source can include any useful material, such as, e.g., various monosaccharides (e.g., dextrose, fructose, galactose, glucose, maltose, xylose, etc.), oligosaccharides, polysaccharides (e.g., cellulose, hemicellulose, starch, etc.), cellulosic material, fatty acids (e.g., saturated or unsaturated fatty acids), biomass hydrolysates, metabolic intermediates (e.g., acetate, lactate, succinate, etc.), alcohols and sugar alcohols (e.g., ethanol, ethylene glycol, glycerol, inositol, malitol, mannitol, sorbitol, or xylitol), lignin and lignin compounds (e.g., lignocellulose and lignocellulosic material), plants and plant products (e.g., corn, liquefied corn meal, corn steep liquor (a byproduct of corn wet milling process that contains nutrients leached out of corn during soaking), corn stover, corn fiber, rice straw, woody plants, herbaceous plants, molasses, etc., which can be found in, for example, in the stems, leaves, hulls, husks, and cobs of plants; or in the leaves, branches, and wood of trees), herbaceous material, agricultural residues, forestry residues, municipal solid wastes, waste paper, as well as pulp and paper mill residues, or mixtures thereof.

EXAMPLES

Example 1: Engineered Hosts with Fungal Ligninases to Depolymerize Lignin

Lignin is a valued source of renewable aromatics, and utilization of lignin for the production of high value aromatics could enable biofuel industries to become cost competitive with petrochemicals. The potential U.S. market for a lignin-derived octane enhancer alone is estimated to be 2.2 billion gallons per year. In addition, lignin forms the second most abundant biopolymer on earth providing an abundant resource for the production of renewable aromatics.

On the other hand, lignin is a complex aromatic heteropolymer and therefore, is very difficult to break down. In nature, the degradation of lignin in the cell walls of dead plant materials happens mainly through enzymes (e.g., laccases and peroxidases) secreted by the Basidiomycetes white-rot fungi. However, this process can be very slow and, therefore, an alternative approach is required for the faster breakdown of lignin into high-value aromatics.

We propose engineering a suitable chassis with fungal ligninases by employing improved synthetic biology tools for the efficient secretion of these ligninolytic enzymes into the extracellular media. A desired characteristic of the bacterial host for this work is to secrete the lignolytic enzymes into the extracellular medium. Gram-positive bacteria have been well recognized to secrete large amounts of proteins into the culture medium. Amongst the gram-positive bacteria, *Bacillus subtilis* is a fast-growing organism and has a relatively well-developed set of molecular tools (e.g. vectors, promoters) for the expression of heterologous proteins. In addition, about 173 different signal peptides have been identified in *B. subtilis*, thereby offering us an expansive library for the selection of an optimal signal peptide for each target protein. For this reason, *B. subtilis* can be a useful host to study heterologous protein expression.

Furthermore, a growth study performed with *B. subtilis* in the presence of depolymerized lignin (DP lignin) demonstrated no significant growth inhibition in the presence of 1 g/L of phenolics such as vanillin and guaiacol. Also, growing *B. subtilis* in the presence of yeast extract, glucose, and $^{13}C$ vanillin, confirmed that vanillin is not its preferred carbon substrate. For all these reasons, initial studies included use of *B. subtilis* as a host for the accumulation of aromatics that would be generated from the depolymerization of lignin and for the heterologous expression and secretion of laccase and peroxidase. Other hosts can be envisioned and are encompassed by the present invention.

In the study conducted in our lab, we have demonstrated microbial depolymerization of lignin by a *B. subtilis* that was engineered for the secretion of an evolved versatile peroxidase. The described invention can be extended to any microorganisms that possess tools for genetic engineering. Some of the other microbes that can be engineered with the fungal ligninases may include, for example and without limitations, *Escherichia coli, Clostridium species, Pseudomonas species, Rhodococcus* species, yeast, etc. Codon optimization may be employed to improve protein expression in the engineered host through modification of the nucleotide sequence. Therefore, the nucleotide sequence may be extended to any sequence whose gene products will give rise to catalytic activity of the fungal ligninases. The promoters and the RBS employed for expression of laccase and peroxidase may vary from host to host. Furthermore, the heterologous genes can be duplicated in the same host to achieve high levels of production of the heterologous enzymes. Additional details follow.

Example 2: Recombinant *B. subtilis* for Depolymerization of Lignin with Evolved Laccase and Peroxidases The laccase and peroxidase chosen for this work were evolved in *Saccharomyces cerevisiae* for improved activity, thermostability, and tolerance to high pH by Professor Miguel Alcalde's research group in the Institute of Catalysis, Spain. The laccase variant (Chu-B) was the result of 12 generations of evolution and the versatile peroxidase variant (2-1B) was obtained after 6 rounds of directed evolution. The evolved laccase and peroxidase demonstrated improvements in enzyme activity by ~41000-fold and 87-fold, respectively, in comparison to the parent enzyme.

Various *B. subtilis* strains were constructed in this study by transforming the WB800N strain (Table 1). The laccase variant showed 100-fold higher activity than its parent enzyme with stability at neutral pH (FIG. 3). Similarly, the peroxidase variant was highly thermostable with $T_{50}$ of 66° C. with stable pH between 7 to 8.

TABLE 1

| Sr. No. | Strain | Genes |
| --- | --- | --- |
| 1 | SS01 | lac ChuB |
| 2 | SS02 | lac ChuB (codon optimized genes) |
| 3 | SS03 | vp 2-1B |
| 4 | SS04 | vp 2-1B (codon optimized genes) |
| 5 | AVNE | Negative control (empty vector, no foreign genes) |

Example 3: Degradation of 2,2'-azino-bis(3-ethyl-benzothiazoline-6-sulphonic Acid) (ABTS) by Recombinant Strains ABTS has been used as a substrate to estimate the antioxidant activity in many previous studies for comparative analysis of different enzymes (see, e.g., Miller N J et al., "Factors influencing the antioxidant activity determined by the ABTS' radical cation assay," *Free Radic. Res.* 1997; 26:195-9; Müller L et al., "Comparative antioxidant activities of carotenoids measured by ferric reducing antioxidant power (FRAP), ABTS bleaching assay (αTEAC), DPPH assay and peroxyl radical scavenging assay," *Food Chem.* 2011; 129:139-48; and Re R et al., "Antioxidant activity applying an improved ABTS radical cation decolorization assay," *Free Radic. Biol. Med.* 1999; 26:1231-7). The engineered *B. subtilis* strains were grown in 2YTG media to assess the activity of laccase and peroxidase. The supernatants were collected one day after induction and were analyzed for the presence of either laccase or versatile peroxidase with ABTS as the substrate. $H_2O_2$ was included in the reactions that were conducted with supernatants from SS03 and SS04 to detect the presence of versatile peroxidase.

As shown in FIG. 3, highest ABTS product absorbance was observed in SS04, which was 100-fold higher than its parent strain. SS04 was codon optimized peroxidase which showed enzyme activity of 58 mU/mL. SS04 strain exhibited three-fold higher absorbance than all the other three strains and control AVNE which proved improved enzyme secretion in SS04 strain. Also, the high enzyme activity was observed only when the reactions were conducted at an acidic pH of 4.

Figure 4A:
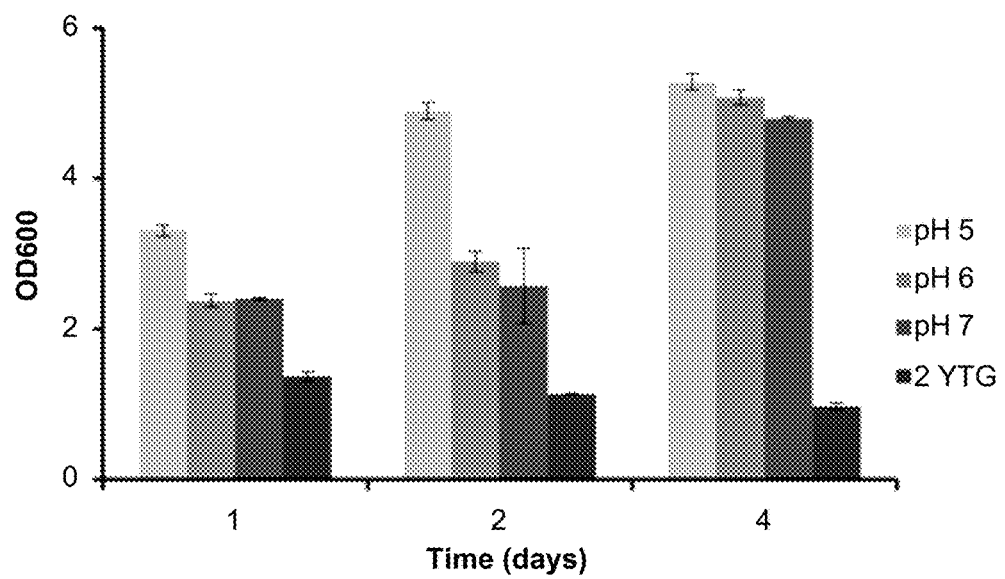
FIGS. 4A-4B provide the effect of pH on growth and activity of the SS04 strain. (A) Growth of SS04 in the specially designed Super rich media (SRM). (B) Enzyme assay with ABTS as substrate confirms the presence of versatile peroxidase activity in the supernatants of SS04 grown in SRM medium.
Figure 4B:
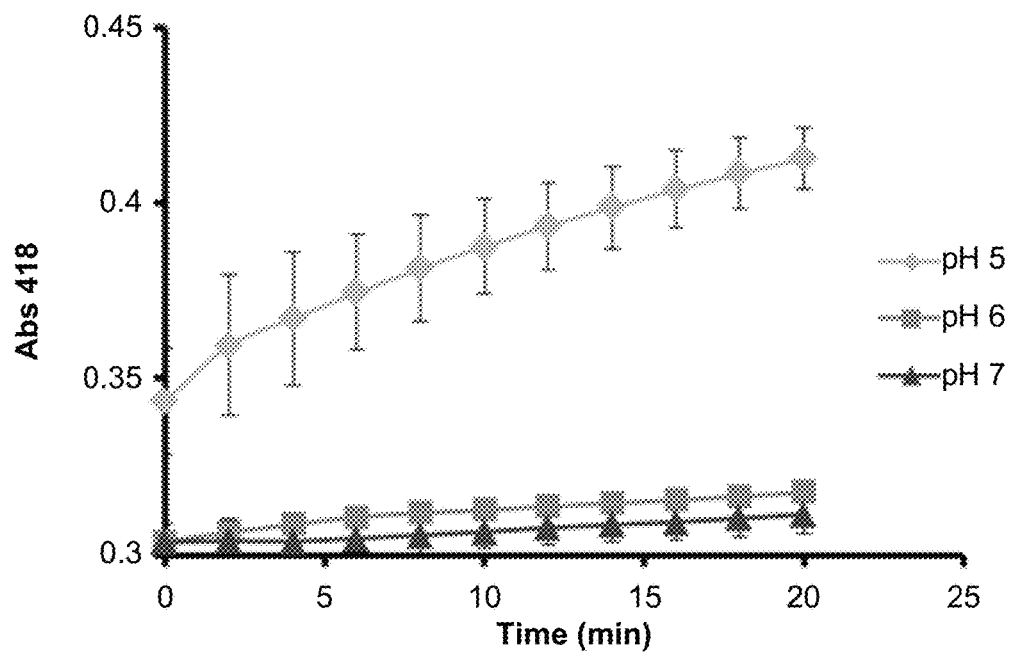

The enzyme activity reduced drastically at a pH of 5. At a pH of 7, enzymatic activity was not observed. However, under normal laboratory conditions, *B. subtilis* is grown under neutral to basic pH. To overcome this challenge, a specialized media was designed (Super rich media, SRM) for both encouraging the growth and secretion of enzyme in SS04. By including citric acid buffer, a pH of 5 can be maintained in the media, and this could enable the enzyme to be active in the extracellular environment. The growth of *B. subtilis* in the SRM medium and the secretion of versatile peroxidase into the extracellular medium can be verified from FIGS. 4A-4B.

Example 4: Lignolysis in SS04 by Gel Permeation Chromatography (GPC) Analysis Lignin degradation by SS04 strains was studied further to confirm lignolysis by SS04. Lignin degradation product treated by SS04 and AVNE was passed through gel permeation chromatography (GPC) to confirm effect of both these strains on the substrate.

Figure 5:
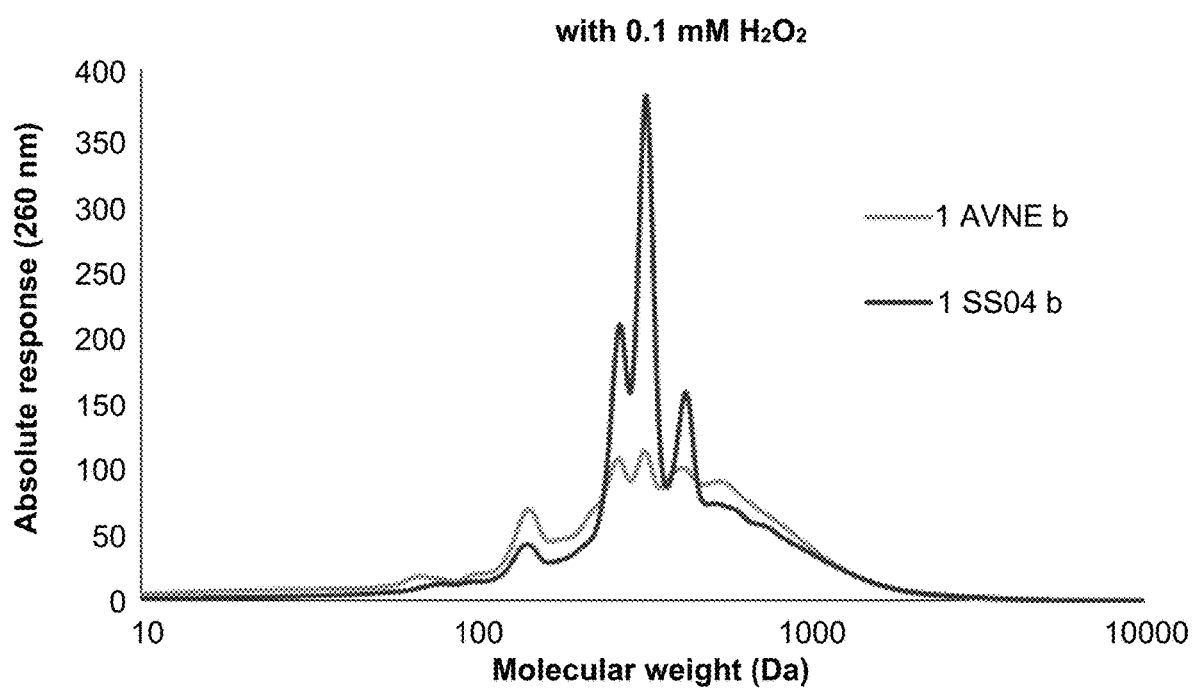
FIG. 5 shows gel permeation chromatography/size exclusion chromatograph (GPC/SEC) analysis of supernatants from the cultures of engineered strains grown in the presence of 10 g/L of lignin.

To demonstrate depolymerization of lignin by engineered bacteria, SS04 and AVNE strains were grown in SRM media at a pH of 5 and in the presence of 10 g/L of lignin (Sigma Aldrich). The supernatants collected 5 days after induction were analyzed for depolymerization by using GPC. From FIG. 5, it can be seen that at ~300 Da, SS04 has a peak that is much higher in comparison to the peak present in the AVNE supernatants. Without wishing to be limited by mechanism, we hypothesize that this could be the result of aromatic monomers that were released from the lignin as a result of versatile peroxidase activity in the extracellular medium. Similar higher, low molecular weight peaks were observed repeatedly in few of the other SS04 biological replicates that were grown with and without hydrogen peroxide.

Figure 6:
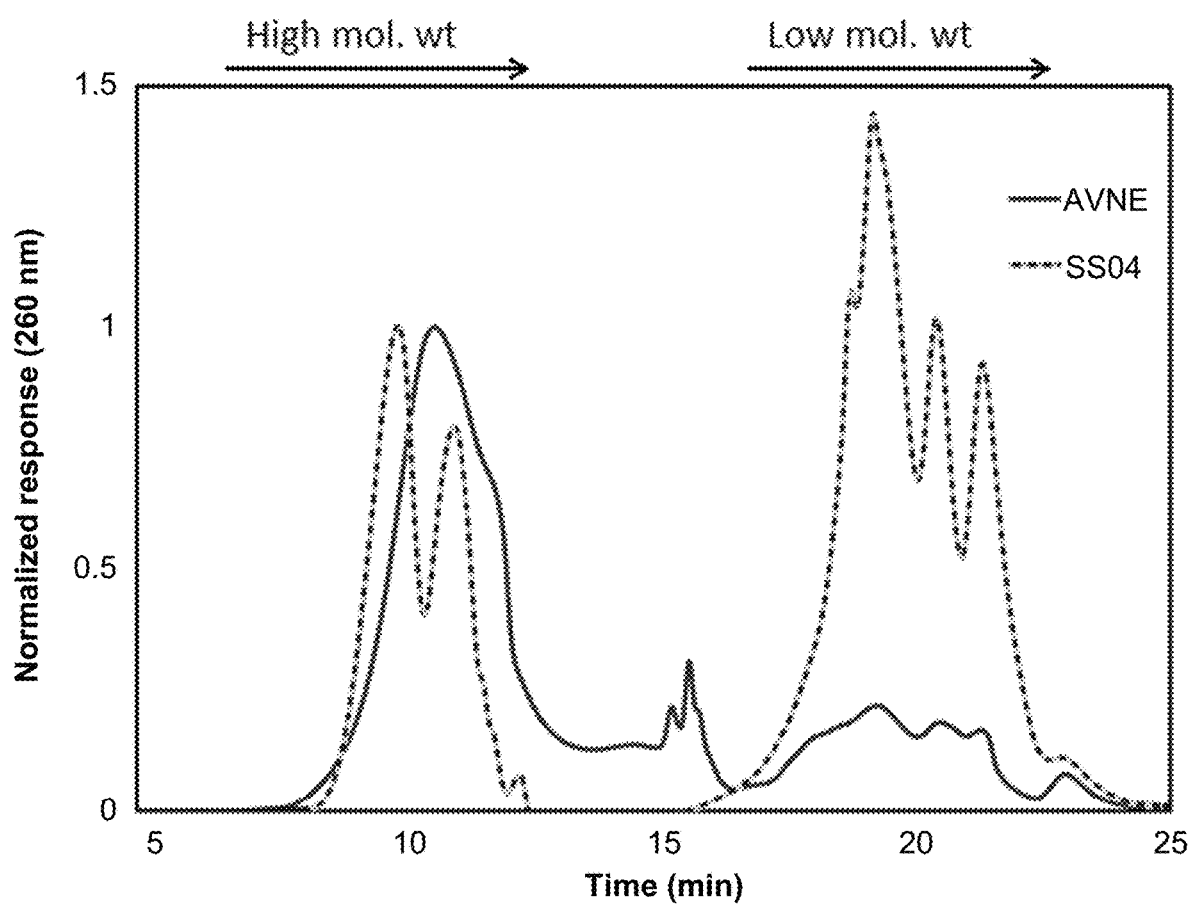
FIG. 6 shows GPC analysis to confirm lignolysis by the SS04 strain.

AVNE being negative control showed no significant breakdown with GPC peaks in the range of high molecular weight (FIG. 6, solid lines). On contrary, SS04 treated product showed peaks in low molecular weights which confirms noteworthy collapse in molecular weight of the substrate (FIG. 6, dashed lines). GPC results demonstrate reduction in substrate size after its treatment with SS04 strain. Further investigation was conducted to identify the aromatic compounds that are present in the supernatants obtained from the cultures of SS04.

Example 5: Presence of Organic Compounds in Depolymerized Substrate

Figure 7:
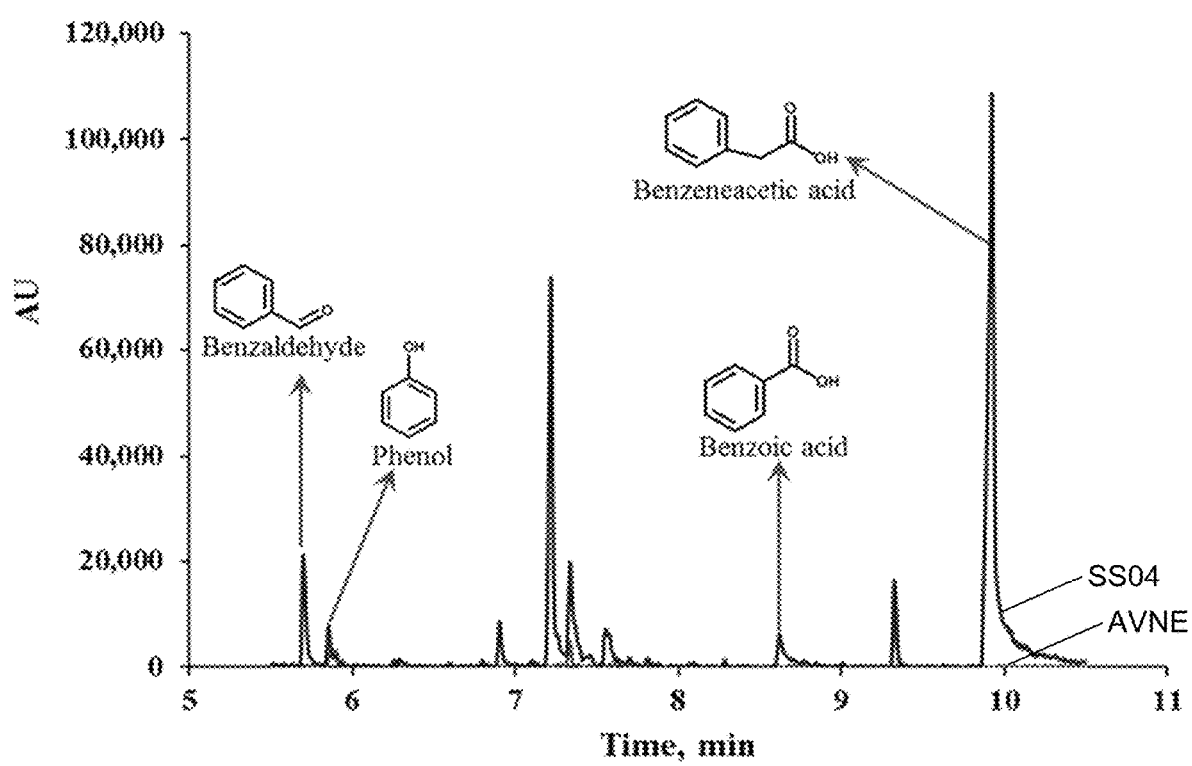
FIG. 7 shows gas chromatography-mass spectrometry (GC-MS) analysis to confirm depolymerization by the SS04 strain.

Additional confirmation of lignolysis in SS04 was studied by gas chromatography-mass spectrometry (GC-MS) of the lignin degradation product. Lignin is a complex organic biopolymer formed from organic compounds, and GC-MS analysis was used to study the presence of organic compounds (see, e.g., Lu Y et al., "Structural characterization of lignin and its degradation products with spectroscopic methods," *J. Spectroscopy* 2017; 2017:8951658 (15 pp.)). GC-MS analysis of lignin degradation products treated by SS04 displayed the presence of organic compounds, like benzaldehyde, phenol, benzoic acid, etc. (FIG. 7). The AVNE strain (negative control) was used to treat same substrate and exhibited insignificant peaks. Presence of organic compounds in degradation product only in case of SS04 further confirmed substantial degradation of lignin by SS04 strain.

Figure 8A:
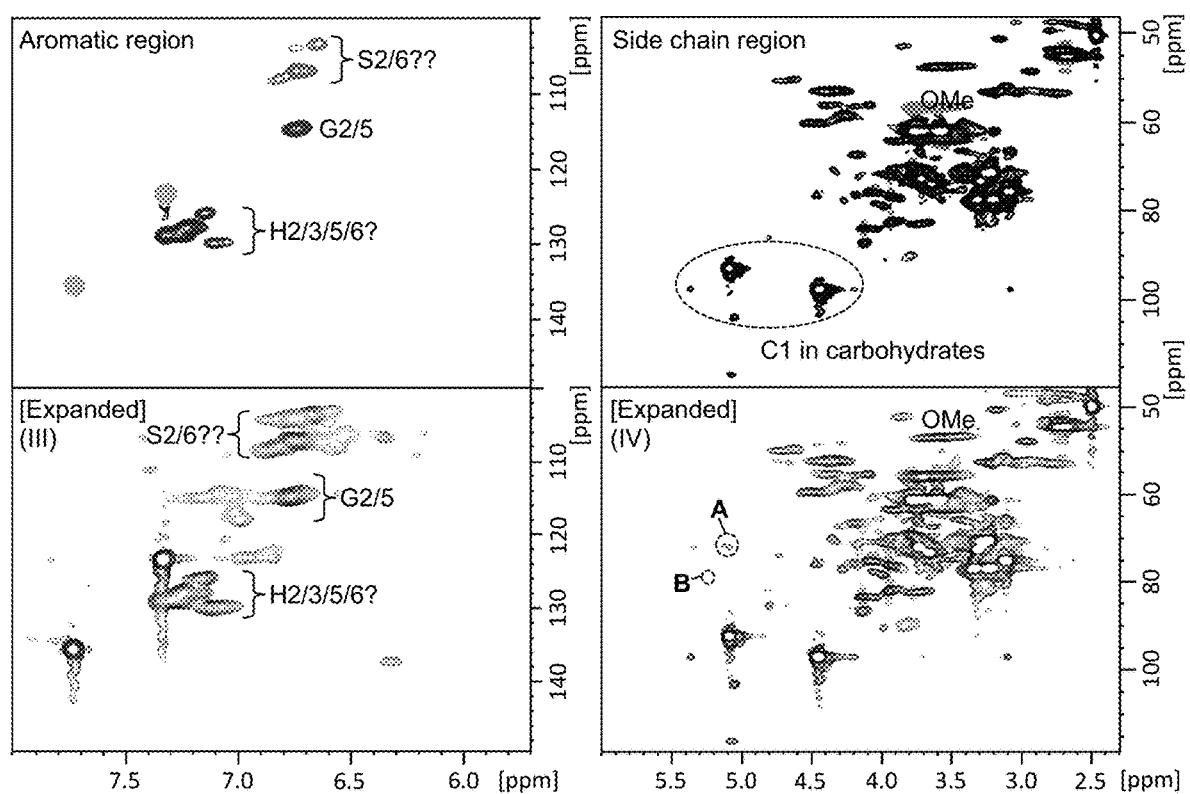
FIGS. 8A-8C show heteronuclear single quantum coherence nuclear magnetic resonance (HSQC NMR) spectra of (A) SRM with lignin at t=0, (B) supernatant of a sample including the AVNE strain, post-degradation, and (C) supernatant of a sample include the SS04 strain, post-degradation.

Example 6: Heteronuclear Single Quantum Coherence Nuclear Magnetic Resonance (HSQC NMR) Analysis of Lignin and Lignin Degradation Products Lignin samples and their derivatized products by SS04 were analyzed by HSQC NMR spectroscopy to identify the principal intermonomeric units in lignin and to study changes in structure after treatment with recombinant strains. HSQC NMR spectra showed prominent p-hydroxyphenyl (H) cross peak derived from guaiacyl (G) unit by demethoxylation. Several cross peaks at $d_{H/C}$ 6.6-6.9/102-110 ppm were evident and, usually, syringyl (S) aromatic appeared in this region. Aryl glycerol-β-aryl ether (β-O-4) and phenyl coumaran (β-5) units were cleaved in the SRM+ lignin sample, t=0 (FIG. 8A).

Figure 8B:
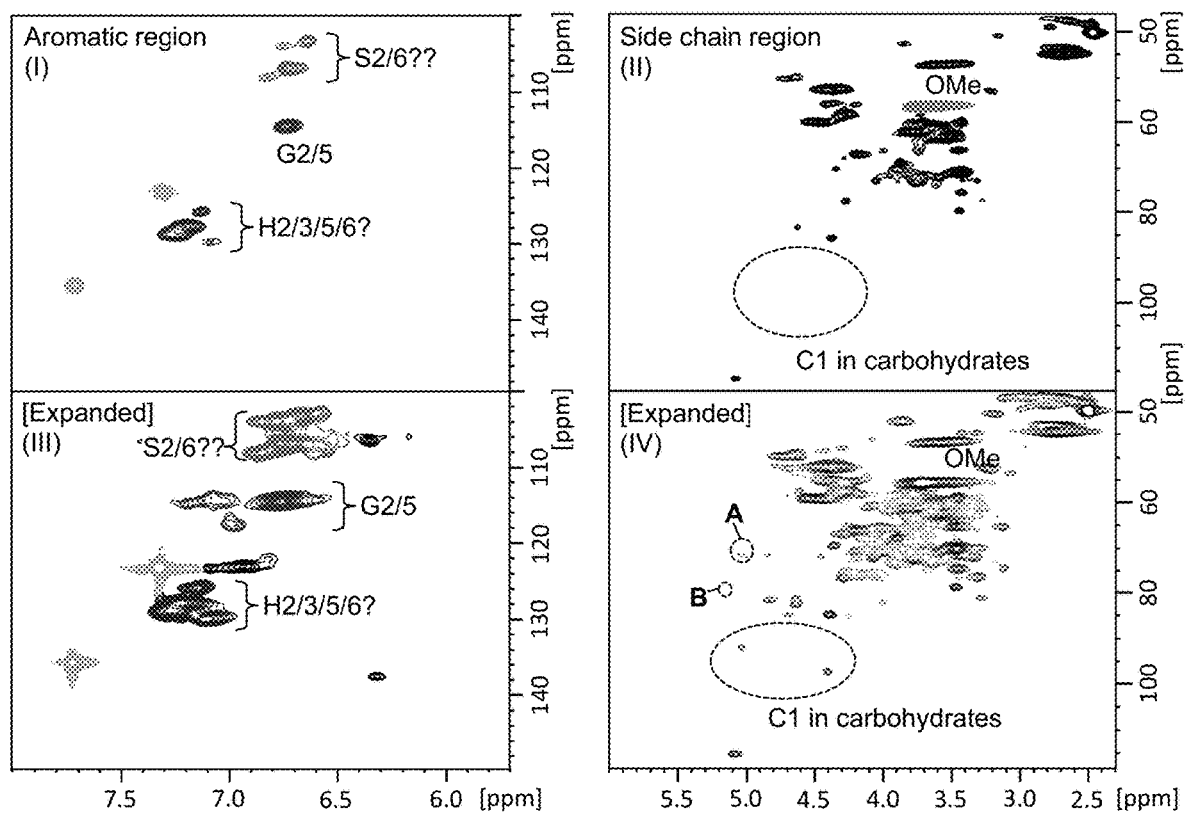

The SRM+lignin sample was treated with the AVNE strain, and its HSQC NMR spectra (FIG. 8B) was studied to understand the structural change in substrate after cultured with AVNE strain. β-O-4 and β-5 peaks disappeared in AVNE supernatant at the same contour level as observed in the SRM+lignin sample (t=0), but some β-O-4 and β-5 units were evident in the expanded spectrum. We also observed a significant decrease in carbohydrate peaks in side chain region, which showed low levels of degradation. In the aromatic region, both hydroxyphenyl (H2/3/5/6) and syringyl (S2/6?) peaks appeared with similar peak integration to that in the SRM+lignin sample (t=0).

Figure 8C:
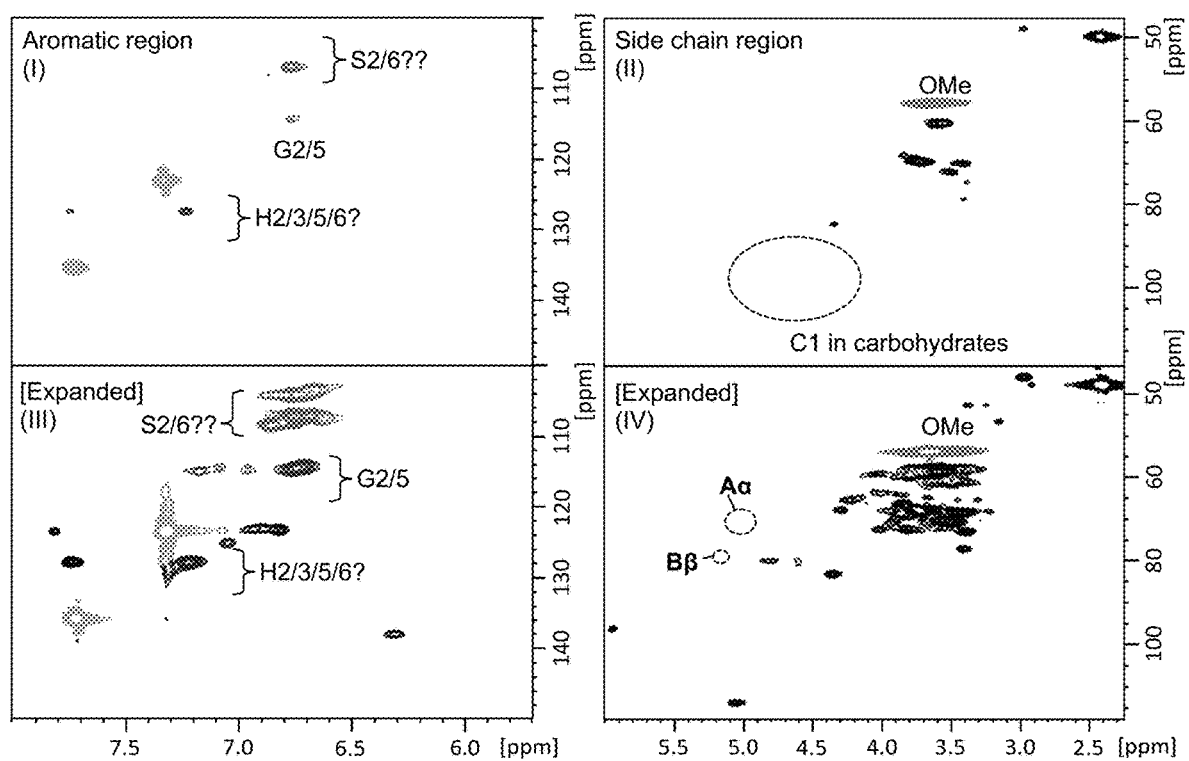

As shown in FIG. 8C, HSQC NMR spectra showed disappearance of many peaks that were observed in the SRM+lignin sample at the same contour levels. β-O-4 and β-5 peaks disappeared in SS04-supernatant at the same contour level as the SRM+lignin sample at t=0 [I] and in the expanded spectrum [IV]. Carbohydrate peaks in the side chain region decreased more than those observed in spectra for both the AVNE-supernatant sample and the SRM+lignin sample (t=0) [II]. In the aromatic region, all aromatic peak decreased with both the AVNE-supernatant sample and the SRM+lignin sample (t=0) [I]. In the expanded aromatic region [III], the all cross peaks of H2/3/5/6, G2/5 and S2/6? also decreased, as compared to the AVNE-supernatant sample and the SRM+lignin sample (t=0).

Significant disappearance of peaks in the β-O-4 and β-5 region, aromatic region, and carbohydrate region illustrate distinct breakdown of the substrate by SS04 strain compared to AVNE control strain. Thus, it can be concluded that SS04 strain demonstrates higher lignin degradation activity, as compared to the control.

Other Embodiments

All publications, patents, patent applications, and accession no. entries mentioned in this specification are incorporated herein by reference to the same extent as if each independent publication or patent application or accession no. entry was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An engineered *Bacillus* host comprising one or more exogenous nucleic acid sequences, wherein at least one exogenous nucleic acid sequence encodes a fungal laccase and a fungal peroxidase;
    wherein the laccase comprises an amino acid sequence having at least 90% sequence identity to one of SEQ ID NOs: 1-4, 10, and 11;
    wherein the peroxidase comprises an amino acid sequence having at least 80% sequence identity to one of SEQ ID NOs: 20-25; and
    wherein the at least one exogenous nucleic acid sequence encodes the peroxidase in a sequence that is codon-optimized for the host.

2. The host of claim 1, wherein the peroxidase is a versatile peroxidase.

3. The host of claim 1, wherein the at least one exogenous nucleic acid sequence encodes the laccase and the peroxidase in a sequence that is codon-optimized for the host.

4. The host of claim 1, wherein the laccase comprises an amino acid sequence having at least 97% sequence identity to one of SEQ ID NOs: 1-4, 10, and 11.

5. The host of claim 1, wherein the peroxidase comprises an amino acid sequence having at least 97% sequence identity to one of SEQ ID NOs:20-25.

6. A method of treating lignin or a derivative thereof, the method comprising:
    providing an engineered microbial host comprising one or more exogenous nucleic acid sequences, wherein at least one exogenous nucleic acid sequence encodes a laccase and a peroxidase; and
    introducing the engineered microbial host to a source comprising lignin or a derivative thereof at a pH of from about 4 to 5;
    wherein the laccase comprises an amino acid sequence having at least 90% sequence identity to one of SEQ ID NOs: 1-4, 10, and 11;
    wherein the peroxidase comprises an amino acid sequence having at least 80% sequence identity to one of SEQ ID NOs: 20-25;
    wherein the host is a member of the genus *Bacillus*; and
    wherein the at least one exogenous nucleic acid sequence encodes the peroxidase in a sequence that is codon-optimized for the host.

7. The method of claim 6, wherein the laccase comprises an amino acid sequence having at least 97% sequence identity to one of SEQ ID NOs: 1-4, 10, and 11.

8. The method of claim 6, wherein the peroxidase comprises an amino acid sequence having at least 97% sequence identity to one of SEQ ID NOs:20-25.

9. The method of claim 6, wherein the host is a *Bacillus subtilis* bacterium.

10. The method of claim 6, wherein the one or more exogenous nucleic acid sequences is provided as an expression vector.

11. The method of claim 6, wherein the pH is 4 to 5.

12. The method of claim 6, wherein the source comprises a media comprising a citric acid buffer.

13. The method of claim 6, wherein the source comprises lignin.

14. The method of claim 13, wherein the source comprises one or more~-O-4 linkages.

15. The method of claim 6, wherein the peroxidase comprises an amino acid sequence having at least 99% sequence identity to any one of SEQ ID NOs: 20-25.

16. The method of claim 6, wherein the laccase comprises an amino acid sequence having at least 99% sequence identity to one of SEQ ID NOs: 1-4, 10, and 11.

17. A method of treating lignin, the method comprising:
    providing an engineered microbial host comprising one or more exogenous nucleic acid sequences, wherein at least one exogenous nucleic acid sequence encodes a laccase and/or a peroxidase; and
    introducing the engineered microbial host to a source comprising lignin at a pH of from about 4 to about 6;
    wherein the source comprises a media comprising a citric acid buffer;
    wherein the host is a member of the genus *Bacillus*;
    wherein the at least one exogenous nucleic acid sequence encodes at least the peroxidase, the peroxidase comprising an amino acid sequence having at least 99% sequence identity to one of SEQ ID NOs: 20-25; and
    wherein the at least one exogenous nucleic acid sequence encodes the peroxidase in a sequence that is codon-optimized for the host.

18. The method of claim 17, wherein the source comprises corn liquefied corn meal, corn steep liquor, corn stover, or corn fiber.

19. The method of claim 17, wherein the peroxidase is one of SEQ ID NOs: 20-25.

20. The method of claim 17, wherein the pH is about 4 to 5.

* * * * *